United States Patent [19]

Bliesener et al.

[11] 4,288,449
[45] Sep. 8, 1981

[54] N-ARYLSULFONYLPYRROLES, THEIR PREPARATION, AND THERAPEUTIC AGENTS CONTAINING THESE COMPOUNDS

[75] Inventors: Jens-Uwe Bliesener, Deidesheim; Karl-Heinz Geiss, Beindersheim; Dieter Lenke, Ludwigshafen; Claus D. Mueller, Viernheim, all of Fed. Rep. of Germany

[73] Assignee: BASF Aktiengesellschaft, Fed. Rep. of Germany

[21] Appl. No.: 154,036

[22] Filed: May 28, 1980

Related U.S. Application Data

[63] Continuation of Ser. No. 58,257, Jul. 17, 1979, abandoned.

[30] Foreign Application Priority Data

Jul. 20, 1978 [DE] Fed. Rep. of Germany ....... 2831850
Apr. 11, 1979 [DE] Fed. Rep. of Germany ....... 2914615

[51] Int. Cl.³ .................. A61K 31/40; C07D 207/48
[52] U.S. Cl. .............................. 424/274; 260/245.7; 260/326.25; 260/326.35; 260/326.36; 260/326.47; 424/263; 424/267; 546/208; 546/275
[58] Field of Search .............. 260/326.35, 326.36, 260/326.25, 326.47; 424/274

[56] References Cited

U.S. PATENT DOCUMENTS

| | | | |
|---|---|---|---|
| 3,709,917 | 1/1973 | Ziegler et al. | 260/326.35 |
| 3,806,534 | 4/1974 | Feit | 424/275 |
| 3,991,097 | 11/1976 | Bormann et al. | 260/326.35 |
| 4,111,953 | 9/1978 | Bormann et al. | 260/326.35 |

OTHER PUBLICATIONS

M. L. Hoefle et al., J. Med. Chem., 11 (1968), 970 et seq.
W. Liebenow et al, Arzneim.-Forsch., (1975), 240 et seq.

*Primary Examiner*—Donald G. Daus
*Assistant Examiner*—M. C. Eakin
*Attorney, Agent, or Firm*—Keil & Witherspoon

[57] ABSTRACT

Compounds of the formula 1

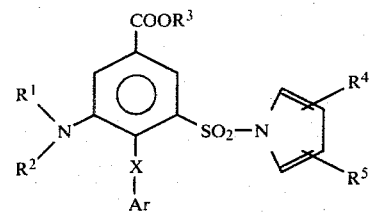

where
$R^1$ is a saturated, unsubstituted or substituted aliphatic radical of 1 to 8 carbon atoms, an unsaturated alkyl radical of 2 to 8 carbon atoms, a cycloalkyl radical of 3 to 7 carbon atoms in the ring or an alkyl radical of 1 to 4 carbon atoms which is substituted by phenyl or by a 5- or 6-membered aromatic heterocyclic ring containing an N, O or S atom, the phenyl ring or the heterocyclic ring itself being unsubstituted, monosubstituted or polysubstituted, and
$R^2$ is hydrogen or
$R^1$ and $R^2$ together with the nitrogen are a 4-membered to 6-membered cycloaliphatic saturated heterocyclic ring,
$R^3$ is hydrogen or alkyl of 1 to 5 carbon atoms,
$R^4$ and $R^5$ are identical or different and each is hydrogen or alkyl of 1 to 5 carbon atoms,
X is oxygen, sulfur or >SO- or >NH- and
Ar is unsubstituted, monosubstituted, disubstituted or trisubstituted phenyl,
and their therapeutically useful ammonium salts, alkali metal salts or acid addition salts, which compounds and salts thereof exhibit valuable pharmacological properties, their preparation, therapeutic agents containing these products, and their use as drugs.

9 Claims, No Drawings

N-ARYLSULFONYLPYRROLES, THEIR PREPARATION, AND THERAPEUTIC AGENTS CONTAINING THESE COMPOUNDS

This is a continuation of application Ser. No. 58,257, filed July 17, 1979, now abandoned.

The present invention relates to compounds of the formula 1

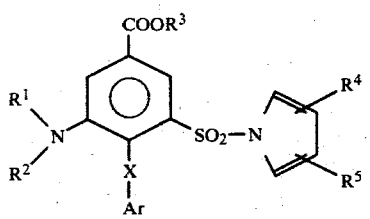

where $R^1$ is a saturated, unsubstituted or substituted aliphatic radical of 1 to 8 carbon atoms, an unsaturated alkyl radical of 2 to 8 carbon atoms, a cycloalkyl radical of 3 to 7 carbon atoms in the ring or an alkyl radical of 1 to 4 carbon atoms which is substituted by phenyl or by a 5- or 6-membered aromatic heterocyclic ring containing an N, O or S atom, the phenyl ring or the heterocyclic ring itself being unsubstituted, monosubstituted or polysubstituted.

$R^2$ is hydrogen or $R^1$ and $R^2$ together with the nitrogen are a 4-membered to 6-membered cycloaliphatic ring, $R^3$ is hydrogen or alkyl of 1 to 5 carbon atoms, $R^4$ and $R^5$ are identical or different and each is hydrogen or alkyl of 1 to 5 carbon atoms, X is oxygen, sulfur or $>SO$- or $>NH$- and Ar is unsubstituted, monosubstituted, disubstituted or trisubstituted phenyl, and their therapeutically useful ammonium salts, alkali metal salts or acid addition salts, which compounds and salts thereof exhibit valuable pharmacological properties, their preparation, therapeutic agents containing these products, and their use as drugs.

Alkyl, alkenyl and cycloalkyl radicals $R^1$ can be, for example, methyl, ethyl, n- and i-propyl, n-, i- and sec.-butyl, n- and i-pentyl, n-hexyl and n-heptyl, allyl, methallyl and 2-butenyl, cyclopropyl, cyclobutyl, cyclopentyl, cyclohexyl and cycloheptyl.

Examples of araliphatic radicals $R^1$ are methylene, 1,2-ethylene and 1,1-ethylene, which bear a phenyl, pyridyl, furyl or thienyl ring, and in which the aromatic or heterocyclic aromatic ring may be monosubstituted or disubstituted by alkyl of 1 to 4 carbon atoms, especially methyl or ethyl, alkoxy of 1 to 4 carbon atoms, especially methoxy and ethoxy, halogen, such as fluorine, chlorine or bromine, nitro, amino, monoalkylamino or dialkylamino, where alkyl is of 1 to 4 carbon atoms, especially dimethylamino or diethylamino, cyano and/or carboxyl.

Examples where $R^1$ and $R^2$ together with the nitrogen form a heterocyclic ring are pyrrolidinyl, piperidinyl and homopiperidinyl.

Alkyl $R^3$ is in particular methyl or ethyl.

$R^4$ and $R^5$ are in particular methyl, ethyl, n- or i-propyl, n-, i- or sec.-butyl or n- or i-pentyl.

Examples of substituted phenyl radicals Ar are phenyl monosubstituted, disubstituted or trisubstituted by alkyl of 1 to 4 carbon atoms, eg. methyl or ethyl, alkoxy of 1 to 4 carbon atoms, eg. methoxy or ethoxy, halogen, eg. fluorine, chlorine or bromine, nitro, amino, or monoalkylamino or dialkylamino where alkyl is of 1 to 4 carbon atoms, eg. dimethylamino or diethylamino.

Preferred compounds of the formula 1, where $R^4$ and $R^5$ are hydrogen are those where $R^1$ is alkyl of 1 to 5 carbon atoms, allyl, benzyl, wherein the phenyl ring is unsubstituted or substituted by methyl, methoxy, carboxyl or bromine, 2- or 3-furylmethyl, wherein the furan ring is unsubstituted or substituted by bromine or methyl, or 2- or 3-thienylmethyl, wherein the thiophene ring is unsubstituted or monosubstituted or disubstituted by methyl, chlorine or bromine, and $R^2$ is hydrogen, or $R^1$ and $R^2$ together with the nitrogen are a pyrrolidine ring, $R^3$ is hydrogen, methyl or ethyl, X is sulfur or oxygen, $>SO$- or $>NH$- and Ar is phenyl, which is unsubstituted or substituted by methyl, chlorine or methoxy, and their therapeutically useful ammonium salts, alkali metal salts or acid addition salts.

Amongst these, particularly preferred compounds are those where $R^1$ is n-butyl, benzyl, 3-thienylmethyl, 2-thienylmethyl or 2-furylmethyl, $R^2$ and $R^3$ are hydrogen, X is sulfur, oxygen or —NH— and Ar is phenyl or p-chlorophenyl.

Further preferred compounds of the formula 1 are those where $R^4$ is methyl or ethyl in the α-position of the pyrrole ring, $R^5$ is alkyl of 1 to 4 carbon atoms in the α'-position of the pyrrole ring, $R^1$ is alkyl of 2 to 5 carbon atoms, benzyl, 2- or 3-thienylmethyl or 2- or 3-furylmethyl, $R^2$ and $R^3$ are hydrogen, X is oxygen or sulfur or -NH- and Ar is phenyl, and their therapeutically useful ammonium salts and alkali metal salts.

Amongst these, particularly preferred compounds are those where $R^1$ is n-butyl, benzyl, 3-thienylmethyl, 2-thienylmethyl, 3-furylmethyl or 2-furylmethyl, $R^2$ and $R^3$ are hydrogen, $R^4$ is methyl or ethyl in the α-position of the pyrrole ring, $R^5$ is methyl, ethyl or n-propyl in the α'-position of the pyrrole ring, X is sulfur, oxygen or NH and Ar is phenyl, and their therapeutically useful ammonium salts and alkali metal salts.

Where $R^3$ is hydrogen, a compound of the formula 1 can be converted in the conventional manner to its ammonium salts or alkali metal salts, especially the sodium salt and potassium salt. Accordingly, the invention also relates to the physiologically safe acid addition salts, prepared, and used, in the conventional manner.

Compounds of the formula 1 may be prepared by a process wherein a compound of the formula 2

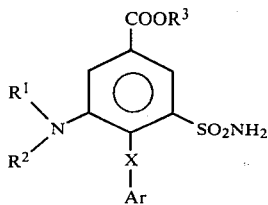

2 where $R^1$, $R^2$, $R^3$, X and Ar have the meanings given for formula 1, is reacted in the conventional manner with a compound of the formula 3

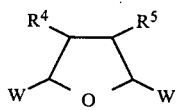

3 where $R^4$ and $R^5$ have the meanings given for formula 1 and W is chlorine, alkoxy of 1 to 5 carbon atoms of alkanoyloxy, with alkyl being of 1 to 5 carbon atoms, or with a compound of the formula 3a

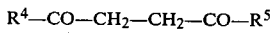  3a where $R^4$ and $R^5$ have the meanings given for formula 1, if appropriate in a solvent and in the presence of an inorganic acid, organic carboxylic acid or sulfonic acid, and, if desired, a resulting carboxylic acid is converted to an ester thereof, a resulting ester is converted to the carboxylic acid, a resulting thioether is converted to the sulfoxide and/or the resulting compound of the formula 1 is converted to a therapeutically useful ammonium salt, alkali metal salt or acid addition salt.

In the starting compounds 3 the radicals W are preferably methoxy, ethoxy, acetoxy or propionyloxy. The particularly preferred starting compound if $R^4$ and $R^5$ are hydrogen is 2,5-dimethoxytetrahydrofuran.

The reaction is preferably carried out in glacial acetic acid or aqueous acetic acid by heating to the boil, as described, for example, by J. W. F. Wasby and K. Chan in Synth. Commun. 3 (1973), 303 et seq. or by A. D. Josey and E. L. Jenner in J. Org. Chem., 27 (1962), 2466-2470.

In another method, the starting compounds 2 and 3 or 3a are reacted in an organic solvent which is inert under the reaction conditions, for example an aromatic hydrocarbon, eg. benzene, toluene, ethylbenzene, chlorobenzene, dichlorobenzene, o-, m- or p-xylene, isopropylbenzene or methylnaphthalene, or an aliphatic or cycloaliphatic hydrocarbon, eg. naphtha, petroleum ether, heptane, hexane, cyclohexane or a mixture of these, and in the presence of a catalytic amount of an inorganic acid, organic carboxylic acid or sulfonic acid, preferably p-toluenesulfonic acid, at from 40° to 200° C., preferably from 60° to 150° C., under atmospheric or superatmospheric pressure.

Amongst the solvents mentioned, cyclohexane and toluene are preferred.

Resulting esters of the formula 1 can be converted to the acid by processes known to those skilled in the art, and conversely, resulting acids can be converted to their esters. Equally, resulting thioethers can be converted in the conventional manner to the sulfoxides.

The starting compounds of the formula 2 are known or can be prepared, for example, in accordance with the processes described in German Laid-Open Applications DOS Nos. 1,964,503 and 2,419,970.

The compounds according to the invention, of the formula 1, where $R^2$ is hydrogen and $R^1$ contains a $CH_2$ group in the alpha position to the N atom (ie. $R^1$ is $R^6$—$CH_2$—, where $R^6$ has the meanings given for formula 4) may also be prepared by a process wherein an acylamino compound of the formula 4

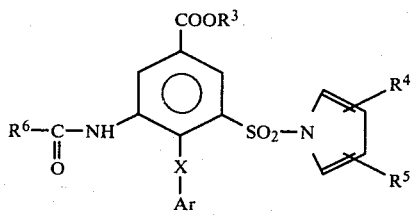

4 where $R^3$ is alkyl of 1 to 5 carbon atoms, $R^4$, $R^5$, X and Ar have the meanings given for formula and $R^6$ is hydrogen or a saturated, unsubstituted or substituted aliphatic radical of 1 to 7 carbon atoms, unsaturated alkyl of 2 to 7 carbon atoms, phenyl or a 5-membered or 6-membered aromatic heterocyclic ring containing an N, O or S atom, the phenyl ring or heterocyclic ring being unsubstituted, monosubstituted or polysubstituted, or alkyl of 1 to 3 carbon atoms which is substituted by phenyl or by a 5-membered or 6-membered aromatic heterocyclic ring containing an N, O or S atom, the phenyl ring or heterocyclic ring being unsubstituted, monosubstituted or polysubstituted, is reduced in the conventional manner with a borohydride in the presence of a Lewis acid and, if desired, a resulting ester is hydrolyzed, a resulting thioether is converted to the sulfoxide and/or a resulting compound is converted to a therapeutically useful ammonium salt, alkali metal salt or acid addition salt.

Not all the compounds according to the invention, of the formula 1, can be prepared by this process. The preferred meanings of $R^6$ are methyl, ethyl, n-propyl, n-butyl, phenyl which is unsubstituted or monosubstituted by methoxy, bromine or methyl, 2- or 3-thienyl which is unsubstituted or monosubstituted or disubstituted in the ring by chlorine, bromine or methyl, or 2- or 3-furyl which is unsubstituted or monosubstituted in the ring by bromine or methyl.

The reduction of the carbonyl group can be carried out, for example, under the conditions described in German Laid-Open Application DOS No. 2,453,548, advantageously in an inert solvent at from −20° C. to 100° C. In the preferred embodiment, the reaction is carried out with diborane in the presence of aluminum chloride, titanium tetrachloride or boron trifluoride or one of its adducts, eg. boron fluoride etherate, as the Lewis acid, in an ether as the solvent.

In a particularly preferred embodiment, the compound of the formula 4 which is to be reduced is dissolved in diethyl ether, tetrahydrofuran or ethylene glycol dimethyl ether as the solvent, together with boron trifluoride or its etherate, and diborane is produced in situ at from 0° C. to 40° C. by adding sodium borohydride as a solid or suspension in a suitable solvent, thereby effecting the reduction.

It is interesting that the reduction takes place without cleavage of the rather labile $SO_2$-N bond and that the pyrrole compound does not undergo any side-reactions in the presence of Lewis acids, as might have been expected under certain circumstances (cf. Gossauer "Die Chemie der Pyrrole", Springer Verlag 1974, pages 324 et seq.).

If desired, the corresponding acids of the formula 1, where $R^3$ is hydrogen, may be obtained in the conventional manner by alkaline or acid hydrolysis of the ester obtained. Preferably, the hydrolysis is carried out in aqueous solution with an equimolar amount of a base, preferably sodium hydroxide solution, at from 20° to 100° C.

Regarding the preparation of intermediates for the starting compounds of the formula 2 and 4, and the preparation of the starting compounds of the formula 2 and 4 themselves, the following may be noted:

4-Halo-3-halosulfonyl-5-nitrobenzoic acid, or one of its alkali metal salts or lower alkyl esters, of the general formula 5

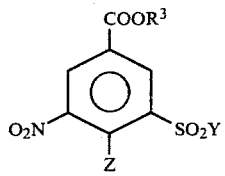

where Y and Z are each halogen, eg. fluorine, chlorine or bromine, and $R^3$ is hydrogen, alkali metal or lower alkyl, especially methyl or ethyl, may be reacted with a pyrrole of the general formula 6

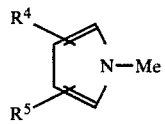

where Me is a metal atom of main group 1 of the periodic table and $R^4$ and $R^5$ have the meanings given for formula 1, in a solvent which is inert under the reaction conditions, at from $-20°$ C. to 200° C., to give a compound of the general formula 7

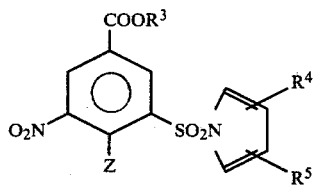

where $R^3$ and Z have the meanings given for formula 5.

Suitable alkali metals Me are lithium, sodium and potassium. Examples of suitable solvents are dimethylsulfoxide, dimethylformamide, N-methylpyrrolidone, tetrahydrofuran, diethyl ether, ethylene glycol dimethyl ether, diethylene glycol dimethyl ether, tetramethylethylenediamine and toluene. The pyrroles of the formula 6 can be prepared in the conventional manner, cf. A. Gossauer "Die Chemie der Pyrrole", Springer-Verlag Berlin, 1974, pages 169 et seq., from pyrrole by reaction with an alkali metal compound in a solvent which is inert under the reaction conditions, preferably in the same solvent as is used for the reaction with a compound 5. Examples of suitable bases are alkali metal alcoholates, alkali metal amides, alkali metal hydrides, alkyl-alkali metal compounds or aryl-alkali metal compounds and the alkali metals themselves, eg. potassium tertiary-butylate, sodium amide, sodium hydride, potassium hydride, n-butyl-lithium, n-butyl-sodium, sodium and potassium.

As is known from the literature, cf. E. P. Papadopoulus and N. F. Haider, Tetra. Lett. 1968, 1721, the reaction of arylsulfonyl chlorides with potassium-pyrrole only takes place satisfactorily if the benzene nucleus is either unsubstituted or carriers, in the p-position, a group exerting a +M-effect, eg. a halogen atom or a $CH_3O$ radical. If a p-nitro group is introduced, the yield drops sharply to 26%, as against 87% in the case of benzenesulfonyl chloride.

It was therefore surprising and unforeseeable that the reaction of the compounds of the formula 5, where the benzene ring carries electronegative groups additional to a nitro group, would also take place in the desired way.

In the preferred embodiment, a pyrrole of the formula 6 is reacted with a compound of the formula 5 in an ether as the solvent, at from 0° C. to 150° C. In a particularly preferred embodiment, a pyrrole 6, where Me is potassium, is reacted with a compound of the formula 5, where $R^3$ is methyl or ethyl and Y and Z are each chlorine, in tetrahydrofuran at from 0° to 80° C. The pyrrole compound 6, where Me is potassium, is prepared by a process known from the literature, as a solution in tetrahydrofuran, from pyrrole and elementary potassium and is reacted further without isolation.

In the next stage, a compound of the general formula 7 is reacted with a compound ArXH, where Ar has the meaning given for formula 2 and X is oxygen, sulfur or $>NH$, to give a N-sulfonylpyrrole of the formula 8

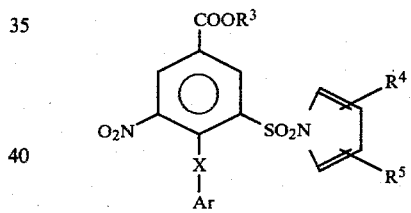

where $R^3$, $R^4$ and $R^5$ have the previously given meanings and X and Ar are as defined above.

Examples of suitable compounds of the formula ArXH are thiophenyl, 2-methylthiophenol, 3-methylthiophenol, 4-methylthiophenol, 4-ethylthiophenol, 2-methoxythiophenol, 3-methoxythiophenol, 4-methoxythiophenol, 4-ethoxythiophenol, 2-chlorothiophenol, 4-chlorothiophenol, 3,4-dichlorothiophenol, 3-dimethylaminothiophenol, 4-dimethylaminothiophenol, 4-aminothiophenol, 4-acetamino-thiophenol, phenol, aniline and phenols and anilines carrying substituents similar to those shown for thiophenol. Any additional functional groups which may be present in ArXH, eg. other OH, $NH_2$ or SH groups, can be blocked by conventional protective groups, for example by acylation.

The reaction can be carried out in the presence or absence of a solvent, the presence of a solvent being more advantageous. Organic solvents, such as ethers and tertiary amides, especially tetrahydrofuran, glycol dimethyl ether, dimethylformamide, N-methylpyrrolidone and hexamethylphosphoric acid triamide, are particularly suitable. The compound ArXH is employed as such, in the presence of a base, or in the form of one of its alkali metal salts. Suitable bases are alkali metal hydroxides, alcoholates, amides and hydrides. The thiophenol and phenol derivatives, which, as already indicated, can be substituted, are of particular importance.

Since it is known that N-acylated pyrroles can very easily undergo cleavage under alkaline conditions, cf. Gossauer, "Die Chemie der Pyrrole", Springer-Verlag, Berlin 1974, page 324, it was not foreseeable that under the above conditions the N-sulfonylpyrrole group would remain preserved. Further, it was surprising that temperatures of above 100° C., as recommended in German Laid-Open Application DOS No. 2,518,999 for the reaction of similar compounds, are not necessary for the replacement of Z by XAr, since the reaction takes place at sufficient speed even below 100° C.

The reaction of a compound 7 is particularly advantageously carried out in an ether, eg. tetrahydrofuran, as the solvent, at from 0° C. to 80° C.

In particular, the sodium or potassium salt of the compound ArXH is used for this reaction, or the reaction is carried out in the presence of a sodium alcoholate or potassium alcoholate, eg. sodium methylate or potassium tertiarybutylate.

A compound of the formula 8, where X is SO, is obtained from the corresponding thioether by oxidation using methods known from the literature, eg. oxidation with $H_2O_2$ or peracetic acid.

The reduction of the nitro group in a compound of the formula 8, to give a compound of the formula 9

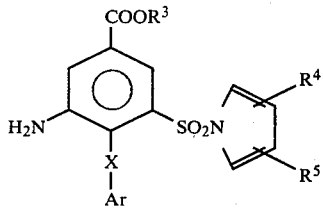

9 where $R^3$, $R^4$, $R^5$, X and Ar have the meanings given for formula 8, is carried out by catalytic hydrogenation in the conventional manner.

The catalytic reduction is carried out in a solvent in the presence of a catalyst, for example palladium, platinum or Raney nickel on a suitable carrier. Preferred solvents are organic solvents, such as methanol, ethanol, ethyl acetate, tetrahydrofuran, dioxane or dimethylformamide. The hydrogenation is carried out at room temperature and atmospheric pressure, or at elevated temperatures, if necessary under pressure in an autoclave, the conditions selected being such that the pyrrole radical remains unaffected by the hydrogenation.

The literature discloses that pyrroles carrying electronegative substituents, for example benzoyl or ethoxycarbonyl, on the nitrogen are easily hydrogenated under mild conditions to give pyrrolidines (cf. J. L. Rainey and H. Adkins, J.Amer.Chem.Soc., 61 (1939), 1104). It was therefore surprising and not forseeable that the hydrogenation of a compound 8 would lead to the desired compound of the formula 9, the pyrrole ring remaining preserved.

A resulting amine of the formula 9 can be reacted with a compound of the general formula $R^6COL$, where $R^6$ has the meanings given in formula 4 and L is halogen, eg. chlorine or bromine, or is the radical of an activated ester or of a mixed or symmetrical anhydride, in which latter case L is O—CO—$R^6$, to give a compound of the formula 4

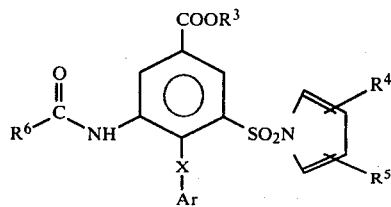

4

Examples of preferred acylating agents are acetyl chloride, n-butyryl chloride, n-butyric anhydride, propionyl chloride, n-valeroyl chloride, benzoyl chloride, 2- or 3-furancarboxylic acid chloride and 2- or 3-thiophencarboxylic acid chloride.

The acylation takes place in the conventional manner but it was not foreseeable that the reaction of the N-sulfonylpyrrole 9 with the compound $R^6COL$ would give pure products of type 4 in good yield, since it is known that pyrroles can also be acylated very easily and it would have been expected that mixtures, which are difficult to separate, would be formed (R. A. Jones and G. P. Bean "The Chemistry of Pyrroles", Acad. Press, N.Y., 1977, pages 159 et seq., and J. Chem. Soc., C, 1970, 2563).

A compound of the general formula 1, where $R^1$ and $R^2$ together with the nitrogen form a heterocyclic ring, can, as described in German Laid-Open Application DOS No. 2,461,601 for the synthesis of similar compounds, also be obtained by reacting an amine of the formula 9 with a compound of the formula 10

$$\underset{L-C-A-C-L'}{\overset{O\phantom{xx}B}{\overset{\|\phantom{xx}\|}{\phantom{x}}}}$$ 10 where A is saturated or unsaturated, straight-chain or branched alkylene of 1 to 5 carbon atoms and B is oxygen or $H_2$, L and L' are identical or different leaving groups, and in particular, when B is O, L and L' are halogen, especially chlorine or bromine, an activated ester group or a mixed anhydride group or L and L' together form a shared O atom, whilst, if B is $H_2$, L has the above meanings and L' may be halogen, eg. chlorine, bromine or iodine, or a sulfonic acid ester group, either in one step or by isolating an intermediate stage of the formula 11

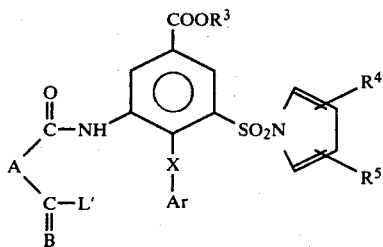

11 where $R^3$, $R^4$, $R^5$, X, Ar, A, B and L' have the above meanings and L' can, where B is O, also be OH, and then cyclizing this intermediate by raising the temperature and/or adding a base, to give a compound of the general formula 12

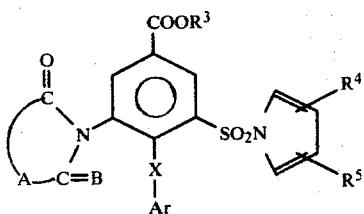

12 where $R^3$, $R^4$, $R^5$, X, Ar, A and B have the above meanings, and then reducing this compound as described above for a compound 4. As in the case of the acylation, described above, of the compound 9 to give the compound 4, it was here again surprising that the desired product 12 could be isolated in a pure form.

According to a further embodiment, a compound of the general formula 7 can, after reduction to the aromatic amine of the general formula 13

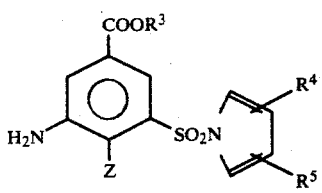

13 where $R^3$, $R^4$, $R^5$ and Z have the meanings given in formula 7, be reacted with a compound of the general formula $R^6$COL to give a compound of the formula 14

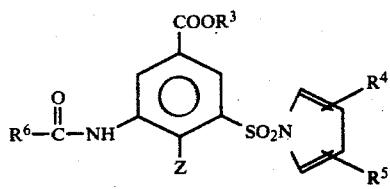

14 where $R^3$, $R^4$, $R^5$ and $R^6$ have the meanings given for formula 4 and Z the meaning given for formula 7, after which this product can be converted to a compound of the formula 4 by reaction with a compound ArXH.

Similarly, a compound of the formula 15

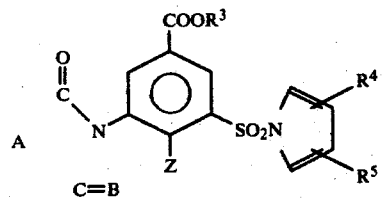

15 where $R^3$, $R^4$, $R^5$, A and B have the meanings given for formula 12 and Z has the meaning given for formula 7, can be prepared by reaction of an amine 13 with a compound 10, and the product can, by subsequent reaction with ArXH, be converted to a compound 12, which is then converted, by the process described above, to a compound according to the invention, of the formula 1, where $R^1$ and $R^2$ together with the nitrogen form a heterocyclic ring.

As regards the conditions of these reactions, and the surprising fact that the reactions succeed, the comments made above in connection with the conversions of the analogous compounds again apply.

Further, a compound of the formula 14 and 15 can be reduced with a borohydride, by the process described above for the conversion of a compound 4 to a compound 1, to give a compound 16

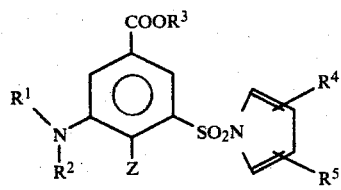

16 where $R^1$ to $R^5$ have the meanings given for formula 1 and Z has the meaning given for formula 7.

Accordingly, a compound of the formula 1 can also be prepared from a compound of the formula 16 by reaction with a compound Ar—X—H, where Ar and X have the above meanings, and the resulting compound can, if appropriate, be hydrolyzed or esterified, or converted to the sulfoxide and/or to a therapeutically useful salt.

In a further embodiment of the present process, a compound of the general formula 17

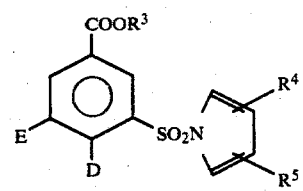

17 where D is Z or XAr and E is one of the radicals $NO_2$, $R^6$CONH or

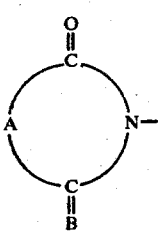

and, if D is Z E may also be

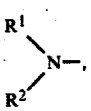

$R^1$, $R^2$, $R^3$, A, B, X, Z and Ar having the meanings given above for formulae 1, 12 and 7, can be prepared by reacting a sulfonamide of the general formula 18 (German Laid-Open Applications DOS No. 1,768,607, DOS No. 1,964,503, DOS No. 2,419,970 and DOS No. 2,453,548)

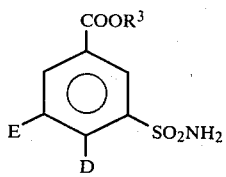

where $R^3$, D and E have the above meanings, with a compound of the formula 3 or 3a, using the process described above. These novel compounds can be employed as intermediates in the various processes mentioned above.

The compounds according to the invention are distinguished by a powerful diuretic action and are therefore particularly suitable for the pharmacotherapy of edemas of various origins, and of high blood pressure. In particular, they can be used as diuretics.

Diuretics containing a sulfonamide group have already been disclosed. Further, it is known that in such compounds the replacement of the two protons on the sulfonamide group leads to a substantial reduction in activity or even complete loss of activity. By contrast, the compounds according to the invention were found, surprisingly, to have a high activity. The fact that the diuretic activity of sulfonamide compounds is reduced by substitution at the amide nitrogen is disclosed in the literature, for example W. Liebenow and F. Leuschner, Arzneim.-Forsch. 25 (1975), 240 et seq., M. L. Höfle et al., J. Med. Chem. 11 (1968), 970 et seq., J. M. Sprague, Ann. N.Y. Acad.-Sci. 71 (1958), 328 et seq. and Handbuch der experimentellen Pharmakologie, Volume XXIV, (1969), page 268 et seq., Springer-Verlag.

The invention also relates to therapeutic agents of formulations which in addition to conventional carriers or diluents contain a compound of the formula 1 as the active compound. The therapeutic agents can be formulated, in accordance with the desired route of administration, by methods known per se to those skilled in the art.

The compounds according to the invention can be administered orally or intravenously, in the conventional manner. The dosage depends on the age, condition and weight of the patient and on the route of administration. As a rule, a daily dose of active compound is from about 0.1 to 100 mg/kg of body weight for oral administration and from about 0.05 to 10.0 mg/kg of body weight for intravenous administration. In special cases it may however be necessary to increase the doses from 5- to 10-fold.

The novel compounds can be employed in the conventional solid or fluid galenical formulations, such as tablets, capsules, powders, granules, dragees or solutions. These are prepared in the conventional manner. For this purpose, the active substances can be compounded with the conventional galenical auxiliaries, eg. talc, gum arabic, sucrose, lactose, cereal starch, corn starch, potato flour, magnesium stearate, alginates, gum tragacanth, carraghenates, polyvinyl alcohol, polyvinylpyrrolidone, aqueous or non-aqueous vehicles, wetting agents, dispersants, emulsifiers and/or preservatives (cf. L. G. Goodman and A. Gilman, The Pharmacological Basis of Therapeutics). The formulations thus obtained normally contain from 0.001 to 99% by weight of the active compound.

The diuretic action was determined on male beagles weighing from 10 to 15 kg.

The animals are kept without food for 18 hours before starting the experiment. 2 hours before administration of the test substance, they are given 20 ml/kg of water orally. The test substances are administered orally as a tragacanth suspension. Thereafter, 4 ml/kg of water are administered 6 times at intervals of 1 hour.

Urine samples are taken by catheterization at intervals of 2 hours, over a period of 6 hours.

In addition to the volume of urine (ml/kg), the excretion of $Na^+$ and $K^+$ (in milliequivalents/kg) is determined photometrically and the excretion of $Cl^-$ (in milliequivalents/kg) is determined coulometrically.

To determine the acute toxicity, the substances are administered orally to groups of 10 female mice of the NMRI strain, weighing from 20 to 23 g. The mean lethal dose (LD 50) is determined after a period of observation of 72 hours.

The comparative substance used is the conventional diuretic Furosemid (4-chloro-N-(2-furylmethyl)-5-sulfamylanthranilic acid).

The compounds of the invention are distinguished by a powerful diuretic action. Table 1 gives the doses producing an increase in $Na^+$ and $H_2O$ excretion similar to that of Furosemid. The substances are from 2.2 (Example 9) to 10 (Examples 114 and 116) times more active than Furosemid. In the case of Furosemid the $Na^+$ excretion no longer rises significantly between the 2nd and 6th hours after administration (from 1,370 to 1,530 $\mu$val/kg), whereas the substances of Examples 9 and 15 show a distinct further increase in excretion, thus having not only better action, but also longer-lasting action, than Furosemid.

The compounds of the invention have higher $Na^+/K^+$ quotients than Furosemid, i.e., the ratio of pharmacotherapeutically desirable increase in $Na^+$ excretion to undesirable increase in $K^+$ excretion is more favorable.

The toxicity of the compounds of the invention in terms of lethal doses administered orally to mice is low (Table 1), resulting in a very substantial interval between the diuretically active dose and the lethal dose.

The lethal dose for Furosemid is 2,000 times higher than the diuretically active dose. In Example 9 it is 2,060 times, in Example 15 6,840 times, in Example 120 more than 10,000 times and in Examples 114 and 116 more than 21,500 times higher than the diuretically active dose.

TABLE 1

| | | | Diuretic action and acute toxicity. Oral administration. | | | | |
| | | | Excretion of electrolyte and of water (dog; 2 hours) | | | | |
| Compound from Sample | Dose mg/kg | Number of animals | $Na^+$ $\mu$val/kg | $K^+$ $\mu$val/kg | $Cl^-$ $\mu$val/kg | $H_2O$ ml/kg | $\dfrac{Na^+}{K^+}$ |
| --- | --- | --- | --- | --- | --- | --- | --- |
| Control animals | — | 60 | 66 | 67 | 81 | 9,3 | 1.0 |
| 9 | 0.464 | 6 | 1,520 | 298 | 1,940 | 27 | 5.1 |
| 15 | 0.215 | 6 | 1,240 | 333 | 1,520 | 23 | 3.7 |

TABLE 1-continued

| | | | | | | | |
|---|---|---|---|---|---|---|---|
| 114 | 0.1 | 6 | 1,410 | 295 | 1,780 | 26 | 4.8 |
| 116 | 0.1 | 6 | 1,150 | 271 | 1,510 | 22 | 4.2 |
| 120 | 0.215 | 6 | 1,260 | 227 | 1,600 | 19 | 5.6 |
| Furosemid | 1.0 | 6 | 1,370 | 449 | 1,720 | 25 | 3.1 |

| Compound from Sample | Dose mg/kg | Number of animals | Excretion of electrolyte and of water (dog; 6 hours) | | | | | Acute Toxicity (mouse) | |
|---|---|---|---|---|---|---|---|---|---|
| | | | Na+ $\mu$val/kg | K+ $\mu$val/kg | Cl− $\mu$val/kg | H$_2$O ml/kg | Na+/K+ | Number of animals | LD$_{50}$ mg/kg |
| Control animals | — | 60 | 212 | 184 | 238 | 27 | 1:2 | — | — |
| 9 | 0.464 | 6 | 2,930 | 810 | 4,200 | 56 | 3:6 | 50 | 957 |
| 15 | 0.215 | 6 | 1,940 | 642 | 2,440 | 45 | 3:0 | 40 | 1,470 |
| 114 | 0.1 | 6 | 1,640 | 442 | 2,080 | 42 | 3:7 | 10 | >2,150[2] |
| 116 | 0.1 | 6 | 1,560 | 473 | 2,100 | 40 | 3:3 | 10 | >2,150[2] |
| 120 | 0.215 | 6 | 2,050 | 527 | 2,760 | 41 | 3:9 | 10 | >2,150[1] |
| Furosemid | 1.0 | 6 | 1,530 | 620 | 1,890 | 39 | 2:5 | 50 | 2,000 |

[1] No mortality after administration of 2,150 mg/g
[2] 1 Animal out of ten died after administration of 2,150 mg/g The Examples which follow are intended to illustrate the invention without implying any limitation. The structures of the compounds in the Examples which follow have been confirmed not only by analytical data but also by spectroscopic methods (IR and NMR).

I. Examples 1 to 113 relate to compounds where $R^4$ and $R^5$, if a pyrrole ring is present, are always hydrogen.

General Procedure (A) A mixture of 15 ml of glacial acetic acid, 1 millimole of a compound of the formula 2 and 1.5 millimoles of 2,5-dimethoxytetrahydrofuran is refluxed. Samples are taken and examined by thin layer chromatography to ascertain the end of the reaction. The reaction mixture is concentrated almost to dryness under reduced pressure and the residue is added to about 20 ml of ice water. The crude product which has separated out is filtered off and dried. In those cases in which the product is obtained as an oil, the aqueous phase is extracted with ethyl acetate. The ethyl acetate phase is then washed with saturated sodium chloride solution, dried over sodium sulfate and concentrated to dryness under reduced pressure. Depending on the purity of the crude product, the compound of the formula 1, is isolated by recrystallization from ethanol or from ethyl acetate/n-hexane, or by column chromatography over silica gel, using methylene chloride/ethyl acetate as the mobile phase. The yields are from 40 to 96%.

The compounds referred to in Examples 1 to 27 below are prepared according to this general procedure.

(B) A mixture of 10 millimoles of a compound of the formula 2, 15 millimoles of 2,5-dimethoxytetrahydrofuran and 0.25 g of p-toluenesulfonic acid in 150 ml of toluene is refluxed under a water separator. Samples are taken and examined by thin layer chromatography to ascertain the end of the reaction. The mixture is then concentrated to dryness under reduced pressure and depending on the purity of the crude product the compound of the formula 1 is isolated by recrystallization from ethanol or ethyl acetate/n-hexane or by column chromatography over silica gel, using methylene chloride/ethyl acetate as the mobile phase.

The compounds referred to in Examples 1 to 27 below are obtained in virtually the same yield as by procedure A.

| Example Number | Formula 1 ($R^3$= H) | | | | Melting point, °C. | Analysis | | | | | | |
|---|---|---|---|---|---|---|---|---|---|---|---|---|
| | $R^1$ | $R^2$ | X | Ar | | | C | H | N | O | S | Cl | Br |
| 1 | C$_2$H$_5$ | H | S | C$_6$H$_5$ | 182–183 | calc. | 56.7 | 4.5 | 6.9 | 15.9 | 15.9 | — | — |
| | | | | | | found | 57.0 | 4.7 | 7.0 | 16.4 | 15.5 | — | — |
| | | | | | | C$_{19}$H$_{18}$O$_4$S$_2$N$_2$ | | | | M = 402.5 | | | |
| 2 | CH$_2$CH$_2$CH$_3$ | H | S | C$_6$H$_5$ | 181–182 | calc. | 57.7 | 4.8 | 6.7 | 15.4 | 15.4 | — | — |
| | | | | | | found | 57.9 | 4.8 | 6.7 | 15.4 | 15.4 | — | — |
| | | | | | | C$_{20}$H$_{20}$O$_4$S$_2$N$_2$ | | | | M = 416.5 | | | |
| 3 | CH$_2$CH=CH$_2$ | H | S | C$_6$H$_5$ | 175–178 | calc. | 57.9 | 4.4 | 6.8 | 15.4 | 15.5 | — | — |
| | | | | | | found | 58.2 | 4.4 | 6.6 | 15.6 | 15.2 | — | — |
| | | | | | | C$_{20}$H$_{18}$O$_4$S$_2$N$_2$ | | | | M = 414.5 | | | |
| 4 | CH$_2$CH$_2$CH$_2$CH$_3$ | H | S | C$_6$H$_5$ | 166–167 | calc. | 58.6 | 5.1 | 6.5 | 14.9 | 14.9 | — | — |
| | | | | | | found | 58.8 | 5.0 | 6.6 | 15.2 | 14.7 | — | — |
| | | | | | | C$_{21}$H$_{22}$O$_4$N$_2$S$_2$ | | | | M = 431 | | | |
| 5 | CH$_2$CH$_2$CH$_2$CH$_3$ | H | O | C$_6$H$_5$ | 166–167 | calc. | 60.8 | 5.4 | 6.8 | 19.3 | 7.7 | — | — |
| | | | | | | found | 61.0 | 5.7 | 6.8 | 19.2 | 7.6 | — | — |
| | | | | | | C$_{21}$H$_{22}$O$_5$N$_2$S | | | | M = 414.5 | | | |
| 6 | CH$_2$CH$_2$CH$_2$CH$_2$CH$_3$ | H | S | C$_6$H$_5$ | 179–182 | calc. | 59.4 | 5.4 | 6.3 | 14.4 | 14.4 | — | — |
| | | | | | | found | 59.7 | 5.5 | 6.5 | 14.2 | 14.1 | — | — |
| | | | | | | C$_{22}$H$_{24}$O$_4$N$_2$S$_2$ | | | | | | | |
| 7 | CH$_2$—CH$_2$<br>\|         \>N<br>CH$_2$—CH$_2$ | | O | C$_6$H$_5$ | 208–210 | calc. | 61.2 | 4.9 | 6.8 | 19.4 | 7.8 | — | — |
| | | | | | | found | 61.1 | 5.1 | 6.7 | 19.3 | 7.7 | — | — |
| | | | | | | C$_{21}$H$_{20}$O$_5$N$_2$S | | | | M = 412 | | | |
| 8 | CH$_2$C$_6$H$_5$ | H | S | C$_6$H$_5$ | 218–220 | calc. | 62.1 | 4.3 | 6.0 | 13.8 | 13.8 | — | — |
| | | | | | | found | 62.1 | 4.4 | 6.1 | 13.6 | 13.4 | — | — |
| | | | | | | C$_{24}$H$_{20}$O$_4$N$_2$S$_2$ | | | | M = 464.6 | | | |
| 9 | CH$_2$C$_6$H$_5$ | H | O | C$_6$H$_5$ | 90–91 | calc. | 62.6 | 5.4 | 5.2 | 20.8 | 6.0 | — | — |

-continued

| Example Number | Formula 1 (R³= H) R¹ | R² | X | Ar | Melting point, °C. | Analysis | | | | | | | |
|---|---|---|---|---|---|---|---|---|---|---|---|---|---|
| | | | | | | | C | H | N | O | S | Cl | Br |
| | | | | | | found | 62.7 | 5.0 | 5.3 | 20.3 | 6.0 | — | — |
| | | | | | | C₂₄H₂₀O₅N₂S · CH₃CO₂C₂H₅ | | | | M = 537.6 | | | |
| 10 | CH₂C₆H₅ | H | SO | C₆H₅ | 218-219 | calc. | 60.0 | 4.2 | 5.8 | 16.6 | 13.3 | — | — |
| | | | | | | found | 59.8 | 4.5 | 5.8 | 16.8 | 13.2 | — | — |
| | | | | | | C₂₄H₂₀O₅N₂S₂ | | | | M = 480.6 | | | |
| 11 | CH₂C₆H₅ | H | S | p-CH₃—C₆H₄ | 212-215 | calc. | 62.7 | 4.6 | 5.9 | 13.4 | 13.4 | — | — |
| | | | | | | found | 62.4 | 4.5 | 5.9 | 13.0 | 13.3 | — | — |
| | | | | | | C₂₅H₂₂O₄N₂S₂ | | | | M = 478.6 | | | |
| 12 | CH₂C₆H₅ | H | S | p-Cl—C₆H₄ | 195-200 | calc. | 57.8 | 3.8 | 5.6 | 12.8 | 12.8 | 7.1 | — |
| | | | | | | found | 57.9 | 3.9 | 5.5 | 13.2 | 12.9 | 7.1 | — |
| | | | | | | C₂₄H₁₉O₄N₂S₂Cl | | | | M = 499 | | | |
| 13 | CH₂C₆H₅ | H | S | p-CH₃O—C₆H₄ | 193-196 | calc. | 60.7 | 4.5 | 5.7 | 16.2 | 13.0 | — | — |
| | | | | | | found | 60.8 | 4.6 | 5.5 | 16.5 | 12.7 | — | — |
| | | | | | | C₂₅H₂₂O₅S₂N₂ | | | | M = 494.6 | | | |
| 14 | CH₂-thienyl | H | S | C₆H₅ | 192-194 | calc. | 56.1 | 3.9 | 5.9 | 13.6 | 20.4 | — | — |
| | | | | | | found | 56.0 | 3.7 | 5.8 | 13.4 | 20.3 | — | — |
| | | | | | | C₂₂H₁₈O₄N₂S₃ | | | | M = 470.6 | | | |
| 15 | " | H | O | C₆H₅ | 174-176 | calc. | 58.1 | 4.0 | 6.1 | 17.6 | 14.1 | — | — |
| | | | | | | found | 58.3 | 4.3 | 6.0 | 17.4 | 13.9 | — | — |
| | | | | | | C₂₂H₁₈O₅N₂S₂ | | | | M = 454.5 | | | |
| 16 | " | H | S | p-Cl—C₆H₄ | 212-214 | calc. | 52.3 | 3.4 | 5.5 | 12.6 | 19.0 | 7.0 | — |
| | | | | | | found | 51.9 | 3.5 | 5.4 | 12.4 | 18.7 | 7.5 | — |
| | | | | | | C₂₂H₁₇O₄N₂S₃Cl | | | | M = 505 | | | |
| 17 | " | H | S | p-CH₃—C₆H₄ | 205-207 | calc. | 57.0 | 4.1 | 5.7 | 13.2 | 19.8 | — | — |
| | | | | | | found | 56.6 | 4.2 | 5.7 | 13.2 | 19.2 | — | — |
| | | | | | | C₂₃H₂₀O₄N₂S₃ | | | | M = 485 | | | |
| 18 | " | H | S | p-CH₃O—C₆H₄ | 191-192 | calc. | 55.2 | 4.0 | 5.6 | 16.0 | 19.2 | — | — |
| | | | | | | found | 55.2 | 4.1 | 5.8 | 16.3 | 19.1 | — | — |
| | | | | | | C₂₃H₂₀O₅S₃N₂ | | | | M = 501 | | | |
| 19 | CH₂-(3,5-dibromothienyl) | H | O | C₆H₅ | 229-230 | calc. | 43.2 | 2.6 | 4.6 | 13.1 | 10.5 | — | 26.1 |
| | | | | | | found | 43.6 | 2.9 | 4.6 | 13.2 | 10.0 | — | 25.4 |
| | | | | | | C₂₂H₁₆49 O₅N₂S₂Br₂ | | | | M = 612 | | | |
| 20 | p-Br—C₆H₄—CH₂ | H | O | C₆H₅ | 197-199 | calc. | 54.7 | 3.6 | 5.3 | 15.2 | 6.1 | — | 15.1 |
| | | | | | | found | 54.6 | 3.9 | 5.3 | 15.6 | 5.9 | — | 15.1 |
| | | | | | | C₂₄H₁₉O₅N₂SBr | | | | M = 527 | | | |
| 21 | p-Br—C₆H₄—CH₂ | H | S | C₆H₅ | 203-204 | calc. | 53.0 | 3.5 | 15.2 | 11.8 | 11.8 | — | 14.7 |
| | | | | | | found | 53.2 | 3.6 | 15.0 | 11.5 | 12.0 | — | 14.5 |
| | | | | | | C₂₄H₁₉O₄N₂S₂Br | | | | M = 543 | | | |
| 22 | p-CH₃O—C₆H₄—CH₂ | H | S | C₆H₅ | 207-208 | calc. | 60.7 | 4.5 | 5.7 | 16.2 | 13.0 | — | — |
| | | | | | | found | 60.6 | 4.6 | 5.6 | 16.2 | 12.7 | — | — |
| | | | | | | C₂₅H₂₂O₅N₂S₂ | | | | M = 495 | | | |
| 23 | o-CH₃O—C₆H₄—CH₂ | H | S | C₆H₅ | 209-210 | calc. | 53.0 | 3.5 | 5.2 | 11.8 | 11.8 | — | 14.7 |
| | | | | | | found | 52.9 | 3.6 | 5.0 | 11.6 | 11.9 | — | 14.5 |
| | | | | | | C₂₄H₁₉O₄N₂S₂Br | | | | M = 543.5 | | | |
| 24 | CH₂-(5-chlorothienyl) | H | S | C₆H₅ | 186-187 | calc. | 52.3 | 3.4 | 5.6 | 12.7 | 19.0 | 7.0 | — |
| | | | | | | found | 52.1 | 3.5 | 5.6 | 12.8 | 18.8 | 7.3 | — |
| | | | | | | C₂₂H₁₇D₄N₂S₃Cl | | | | M = 505 | | | |
| 25 | p-CN—C₆H₄—CH₂ | H | S | C₆H₅ | 118-120 | calc. | 61.3 | 3.9 | 8.6 | 13.1 | 13.1 | — | — |
| | | | | | | found | 61.0 | 4.0 | 8.7 | 13.0 | 12.9 | — | — |
| | | | | | | C₂₅H₁₉O₄N₃S₂ | | | | M = 490 | | | |
| 26 | m-CH₃—C₆H₄—CH₂ | H | S | C₆H₅ | 178-180 | calc. | 62.7 | 4.6 | 5.9 | 13.4 | 13.4 | — | — |
| | | | | | | found | 62.6 | 4.6 | 5.9 | 13.8 | 13.1 | — | — |
| | | | | | | C₂₅H₂₂O₄N₂S₂ | | | | M = 479 | | | |
| 27 | p-CO₂H—C₆H₄—CH₂ | H | S | C₆H₅ | 266-268 | calc. | 59.0 | 4.0 | 5.5 | 18.8 | 12.6 | | |
| | | | | | | found | 59.2 | 4.3 | 5.6 | 18.9 | 12.3 | | |
| | | | | | | C₂₅H₂₀O₆N₂S₂ | | | | M = 509 | | | |

EXAMPLE 28

The compound of Example 8 is converted to the methyl ester in accordance with the following general procedure (C):

(C) 0.2 mole of the carboxylic acid and 800 ml of a mixture of equal parts of methanol and concentrated hydrochloric acid are heated for about 24 hours at 50° C.

The end of the reaction is ascertained by thin layer chromatography. The mixture is then concentrated to dryness under reduced pressure and purified by recrystallization from methanol.

Yields: 70-95%.

Melting point: 151°-154° C.

| C₂₅H₂₂O₄N₂S₂ | | M = 479 | | |
|---|---|---|---|---|
| Analysis: | C | H | O | N | S |
| calculated: | 62.7 | 4.7 | 13.3 | 5.8 | 13.4 |

-continued

| $C_{25}H_{22}O_4N_2S_2$ | | M = 479 | | | |
|---|---|---|---|---|---|
| Analysis: | C | H | O | N | S |
| found: | 62.9 | 4.7 | 13.2 | 5.8 | 13.1 |

EXAMPLES 29 TO 31

The compounds of Examples 29 to 31 are prepared in accordance with the following procedure (D):

(D) 0.02 mole of the thioether of the formula 1 (where $R^3$ is H and X is S), 200 ml of glacial acetic acid and 17 ml of 30% strength hydrogen peroxide are stirred for 2 days at room temperature. The reaction mixture is then added to 1 liter of ice water and the product which has precipitated is filtered off, dried and recrystallized from methanol.

Yield: 70–95%.

| Formula 1: $R^2$ and $R^3$ = H, X = SO | | | |
|---|---|---|---|
| Example No. | $R^1$ | Ar | Melting point, °C. |
| 29 | $C_6H_5$—$CH_2$— | $C_6H_5$ | 218–219 |
| Analysis: | C | H | O | N | S |
| calculated: | 60.0 | 4.2 | 16.6 | 5.8 | 13.3 |
| found: | 59.8 | 4.5 | 16.8 | 5.8 | 13.2 |
| $C_{24}H_{20}O_5N_2S_2$ | M = 480.6 | | | | |
| 30 | $C_6H_5$—$CH_2$— | p-Cl—$C_6H_4$ | 214–215 |
| $C_{24}H_{19}O_5N_2S_2Cl$ | M = 515 | | | | |
| Analysis: | C | H | O | N | S | Cl |
| calculated: | 56.0 | 3.7 | 15.5 | 5.4 | 12.4 | 6.9 |
| found: | 56.1 | 3.8 | 15.8 | 5.6 | 12.4 | 7.0 |
| 31 | 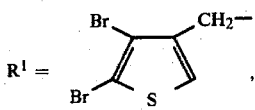 | p-$CH_3$—$C_6H_4$ | 226–227 |
| $C_{23}H_{20}O_5N_2S_3 \times 0.5\ H_2O$ | M = 510 | | | | |
| Analysis: | C | H | O | N | S |
| calculated: | 54.2 | 4.2 | 17.3 | 5.5 | 18.9 |
| found: | 54.7 | 4.3 | 17.4 | 5.7 | 18.7 |

EXAMPLE 32

Formula 1: $R^1 = C_6H_5CH_2$, $R^2 = H$, $R^3 = C_2H_5$, X = SO, Ar = p-Cl-$C_6H_4$.

4 g of the free acid from Example 30 in a mixture of 100 ml of absolute ethanol and 1 ml of concentrated sulfuric acid are refluxed for 8 hours. The solution is then concentrated to 50 ml and the residue is added to 200 ml of ice water.

The crude product which has precipitated is filtered off, washed with water and then with n-hexane, dried and recrystallized from methanol/methylene chloride.

Yield: 90%.
Yield: 3.6 g.
Melting point: 158°–159° C.

| $C_{26}H_{23}O_5N_2S_2Cl$ | | M = 543. | | | |
|---|---|---|---|---|---|
| Analysis: | C | H | O | N | S | Cl |
| calculated: | 57.5 | 4.3 | 14.7 | 5.2 | 11.8 | 6.5 |
| found: | 57.7 | 4.3 | 15.0 | 5.4 | 11.6 | 6.5 |

EXAMPLE 33

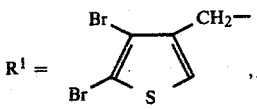

$R^2 = H$, $R^3 = H$, X=O, Ar=$C_6H_5$.

Reaction of 3-amino-4-phenoxy-5-sulfamylbenzoic acid with 4,5-dibromo-3-bromomethyl-thiophene in absolute ethanol, followed by hydrolysis, in accordance with a procedure known from the literature (P. W. Feit, J. Med. Chem. 14 (1971), 432) gives a compound of the formula 2, where $$R^1 = \begin{array}{c} Br \\\\ Br \end{array} \begin{array}{c} CH_2— \\\\ S \end{array}$$

$R^2$, $R^3$ = H, X=O and Ar=$C_6H_5$.
Melting point: 241°–242° C.

| $C_{18}H_{14}O_5N_2S_2Br_2$ | | M = 562 | | | |
|---|---|---|---|---|---|
| Analysis: | C | H | O | N | S |
| calculated: | 38.4 | 2.5 | 14.2 | 5.0 | 11.4 |
| found: | 38.4 | 2.8 | 14.0 | 4.9 | 11.1 |

The compounds of Examples 34 to 39 which follow are prepared similarly to Example 33.

| Formula 2 ($R^2$, $R^3$ = H, Ar = $C_6H_5$) | | | | | | | | | |
|---|---|---|---|---|---|---|---|---|---|
| Example No. | $R^1$ | X | Melting point [°C.] | | Analysis | | | | |
| | | | | | C | H | O | N | S | Cl |
| 34 | p-$CH_3O$—$C_6H_4$—$CH_2$ | S | 234–235 | calc. | 56.7 | 4.5 | 18.0 | 6.3 | 14.4 | |
| | | | | found | 56.8 | 4.8 | 18.3 | 6.4 | 14.4 | |
| | | | | $C_{21}H_{20}O_5N_2S_2$ | | M = 445 | | | | |
| 35 | p-$CH_3O$—$C_6H_4$—$CH_2$ | O | 261–262 | calc. | 58.9 | 4.8 | 22.4 | 6.5 | 7.5 | |
| | | | | found | 58.7 | 5.0 | 22.7 | 6.5 | 7.4 | |
| | | | | $C_{21}H_{20}O_6N_2S$ | | M = 428.4 | | | | |
| 36 | 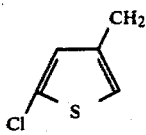 | S | 224–225 | calc. | 47.5 | 3.3 | 14.1 | 6.6 | 21.1 | 7.8 |
| | | | | found | 47.1 | 3.6 | 14.6 | 6.2 | 20.8 | 7.2 |
| | | | | $C_{18}H_{15}O_4N_2S_3Cl$ | | M = 455 | | | | |

-continued

Formula 2 ($R^2$, $R^3$ = H, Ar = $C_6H_5$)

| Example No. | $R^1$ | X | Melting point [°C] | Analysis | | | | | |
|---|---|---|---|---|---|---|---|---|---|
| | | | | C | H | O | N | S | Cl |
| 37 | (5-chloro-2-thienyl)-CH₂— | O | 261–262 | calc. 49.3<br>found 49.9<br>$C_{18}H_{15}O_5S_2N_2Cl$ | 3.4<br>3.6 | 18.2<br>17.9<br>M = 439 | 6.4<br>6.5 | 14.6<br>14.2 | 8.1<br>8.0 |
| 38 | p-Br—$C_6H_4$—$CH_2$ | O | 289–291 | (as the mono-Na salt) | | | | | |
| 39 | p-Br—$C_6H_4$—$CH_2$ | S | 288–290 | (as the mono-Na salt) | | | | | |

Reaction of 3-amino-4-phenoxy (or -phenylthio or -anilino)-5-sulfamylbenzoic acid with the appropriate substituted benzyl bromides in an aqueous phase at a constant pH, in accordance with a procedure known from the literature (P. W. Feit, J. Med. Chem. 14 (1971), 432) is used to prepare some of the compounds of the formula 2. For further data, see under Examples 110 to 113.

EXAMPLE 40

3-Benzylamino-4-phenylthio-5-(pyrrol-1-yl)-sulfonyl)-benzoic acid methyl ester

Formula 1: $R^3 = CH_3$, X = S, Ar = $C_6H_5$, $R^1 = C_6H_5$—$CH_2$—.

1 ml of boron trifluoride etherate, followed by a suspension of 0.24 g of sodium borohydride in 15 ml of absolute ethylene glycol dimethyl ether are added dropwise to a solution of 2.0 g of 3-benzoylamino-4-phenylthio-5-pyrrol-1-yl-sulfonyl-benzoic acid methyl ester in 17 ml of absolute ethylene glycol dimethyl ether, and the mixture is stirred at room temperature. Excess reducing agent is then destroyed with a small amount of water and the product is precipitated by adding 50 ml of water. After filtering off the product, and washing it with water and hexane, 1.8 g of 3-benzylamino-4-phenylthio-5-pyrrol-1-yl-sulfonyl-benzoic acid methyl ester, of melting point 151°–153° C., are obtained. Yield: 95%.

| $C_{25}H_{22}N_2O_4S_2$ | | | M = 479 | | |
|---|---|---|---|---|---|
| Analysis: | C | H | N | O | S |
| calculated: | 62.7 | 4.6 | 5.8 | 13.3 | 13.4 |
| found: | 62.9 | 4.7 | 5.8 | 13.2 | 13.1 |

The compounds of Examples 41–55 are prepared by a procedure similar to that of Example 40, yields of 80–95% being obtained.

Formula 1 ($R^2$ = H, $R^3$ = $CH_3$, Ar = $C_6H_5$)

| Example Number | $R^1$ | X | Melting point, °C | Analysis | | | | | | |
|---|---|---|---|---|---|---|---|---|---|---|
| | | | | C | H | O | N | S | Cl | Br |
| 41 | $C_6H_5CH_2$— | NH | 158–159 | calc. 65.1<br>found 65.0<br>$C_{25}H_{23}O_4N_3S$ | 5.0<br>5.0 | 13.9<br>14.2<br>M = 462 | 9.1<br>9.3 | 6.9<br>6.9 | | |
| 42 | (furan-2-yl)-CH₂ | S | 111–112 | — | | | | | | |
| 43 | (furan-2-yl)-CH₂ | NH | 129–130 | calc. 61.2<br>found 60.9<br>$C_{23}H_{21}O_5N_3S$ | 4.7<br>4.8 | 17.7<br>17.5<br>M = 452 | 9.3<br>9.6 | 7.1<br>7.1 | | |
| 44 | (furan-3-yl)-CH₂— | S | 116–119 | — | | | | | | |
| 45 | (furan-3-yl)-CH₂— | NH | 138–139 | calc. 61.2<br>found 60.9<br>$C_{23}H_{21}O_5N_3S$ | 4.7<br>4.7 | 17.7<br>17.9<br>M = 452 | 9.3<br>9.3 | 7.1<br>7.0 | | |
| 46 | (thien-2-yl)-CH₂ | S | 140–141 | calc. 57.0<br>found 57.1<br>$C_{23}H_{20}O_4N_2S_3$ | 4.2<br>4.3 | 13.2<br>13.3<br>M = 485 | 5.8<br>5.9 | 19.8<br>19.6 | | |
| 47 | (thien-2-yl)-CH₂ | NH | 152–153 | calc. 59.1<br>found 58.8<br>$C_{23}H_{21}O_4N_3S_2$ | 4.5<br>4.5 | 13.7<br>13.7<br>M = 468 | 9.0<br>9.3 | 13.7<br>13.5 | | |
| 48 | (5-bromo-furan-2-yl)-CH₂ | O | 150–151 | — | | | | | | |

-continued

Formula 1 ($R^2$ = H, $R^3$ = CH$_3$, Ar = C$_6$H$_5$)

| Example Number | R$^1$ | X | Melting point, °C. | Analysis | | | | | | |
|---|---|---|---|---|---|---|---|---|---|---|
| | | | | C | H | O | N | S | Cl | Br |
| 49 | 5-bromo-furfuryl | O | 129–130 | calc. 50.5<br>found 50.9<br>C$_{23}$H$_{19}$O$_5$S$_2$Br | 3.5<br>3.9 | 14.6<br>14.5<br>M = 547 | 5.1<br>5.1 | 11.7<br>11.7 | — | 14.6<br>14.5 |
| 50 | 3-methyl-thienyl-CH$_2$ | O | 108–110 | calc. 59.7<br>found 59.5<br>C$_{24}$H$_{22}$O$_5$N$_2$S$_2$ | 4.6<br>4.8 | 16.6<br>16.6<br>M = 482 | 5.8<br>5.7 | 13.3<br>12.9 | | |
| 51 | 5-methyl-furfuryl | O | 124–125 | calc. 61.8<br>found 61.6<br>C$_{24}$H$_{22}$O$_6$N$_2$S | 4.7<br>4.8 | 20.6<br>20.3<br>M = 466 | 6.0<br>6.0 | 6.9<br>6.8 | | |
| 52 | 5-bromo-thienyl-CH$_2$ | S | 141–142 | — | | | | | | |
| 53 | 3-furyl-CH$_2$— | O | 131–132 | calc. 61.0<br>found 60.9<br>C$_{23}$H$_{20}$O$_6$N$_2$S | 4.4<br>4.4 | 21.2<br>21.0<br>M = 452 | 6.2<br>6.1 | 7.0<br>6.9 | | |
| 54 | 5-bromo-furfuryl | NH | 126–127 | calc. 52.1<br>found 52.1<br>C$_{23}$H$_{20}$O$_5$N$_3$SBr | 3.8<br>3.9 | 15.1<br>15.1<br>M = 530 | 7.9<br>8.1 | 6.1<br>6.1 | — | 15.1<br>15.1 |
| 55 | 3-thienyl-CH$_2$— | NH | 149–150 | calc. 59.1<br>found 59.0<br>C$_{23}$H$_{21}$O$_4$N$_3$S$_2$ | 4.5<br>4.7 | 13.7<br>13.5<br>M = 468 | 9.0<br>9.2 | 13.7<br>13.5 | | |

EXAMPLE 56

3-Benzylamino-4-phenylthio-5-(pyrrol-1-yl-sulfonyl)-benzoic acid

Formula 1: $R^1$=C$_6$H$_5$—CH$_2$, $R^2$=H, $R^3$=H, X=S, Ar=C$_6$H$_5$.

A solution of 0.083 g of NaOH in 30 ml of water is added to a solution of 1.0 g of 3-benzylamino-4-phenylthio-5-pyrrol-1-yl-sulfonyl-benzoic acid methyl ester in 70 ml of ethanol, and the mixture is stirred first for 4 hours at room temperature and then for 1 hour at 40° C. to complete the reaction. After stripping off the ethanol under reduced pressure, the aqueous phase is acidified with dilute hydrochloric acid and the product is filtered off and recrystallized from ethyl acetate. 3-Benzylamino-4-phenylthio-5-pyrrol-1-yl-sulfonylbenzoic acid of melting point 218°–220° C. is obtained. Yield: 60%.

EXAMPLES 57–71

The compounds of Examples 41 to 55 are converted to the carboxylic acids of the general formula 1, with $R^2$=H, $R^3$=H, Ar=C$_6$H$_5$, by a procedure similar to Example 56, yields of 60–96% being obtained.

Formula 1 ($R^2$ and $R^3$ = H, Ar = C$_6$H$_5$)

| Example Number | R$^1$ | X | Melting points °C. | Analysis | | | | | | |
|---|---|---|---|---|---|---|---|---|---|---|
| | | | | C | H | O | N | S | Cl | Br |
| 57 | R$^1$ | NH | 228–230 | calc. 64.4<br>found 64.6<br>C$_{24}$H$_{21}$O$_4$N$_3$S | 4.7<br>4.8 | 14.3<br>14.5<br>M = 448 | 9.4<br>9.0 | 7.2<br>7.2 | | |
| 58 | furfuryl | S | 184–185 | calc. 58.1<br>found 57.9<br>C$_{22}$H$_{18}$O$_5$N$_2$S$_2$ | 4.0<br>4.1 | 17.6<br>17.7<br>M = 454.5 | 6.1<br>6.2 | 14.1<br>13.9 | | |
| 59 | furfuryl | NH | 186–187 | calc. 60.4<br>found 60.6<br>C$_{22}$H$_{19}$O$_5$N$_3$S | 4.4<br>4.4 | 18.3<br>18.3<br>M = 437 | 9.6<br>9.9 | 7.3<br>7.3 | | |
| 60 | 3-furyl-CH$_2$— | S | 202–203 | calc. 58.1<br>found 57.9<br>C$_{22}$H$_{18}$O$_5$N$_2$S$_2$ | 4.0<br>4.1 | 17.6<br>18.0<br>M = 454.5 | 6.1<br>6.3 | 14.1<br>13.8 | | |
| 61 | 3-furyl-CH$_2$— | NH | 195–196 | calc. 60.4<br>found 60.3<br>C$_{22}$H$_{19}$O$_5$N$_3$S | 4.4<br>4.6 | 18.3<br>18.6<br>M = 437 | 9.6<br>9.9 | 7.3<br>7.2 | | |

-continued

Formula 1 ($R^2$ and $R^3$ = H, Ar = $C_6H_5$)

| Example Number | $R^1$ | X | Melting points °C. | Analysis | | | | | | |
|---|---|---|---|---|---|---|---|---|---|---|
| | | | | | C | H | O | N S | Cl | Br |
| 62 | thienyl-CH₂ | S | 201–202 | calc. | 56.2 | 3.9 | 13.6 | 6.0 20.4 | | |
| | | | | found | 56.2 | 3.9 | 13.7 | 6.0 19.8 | | |
| | | | | $C_{22}H_{18}O_4N_2S_3$ | | | M = 471 | | | |
| 63 | thienyl-CH₂ | NH | 205–206 | calc. | 58.3 | 4.2 | 14.1 | 9.3 14.1 | | |
| | | | | found | 58.3 | 4.4 | 13.9 | 9.5 13.8 | | |
| | | | | $C_{22}H_{19}O_4N_3S_2$ | | | M = 454 | | | |
| 64 | Br-furyl-CH₂ | O | 169–170 | calc. | 51.1 | 3.3 | 18.6 | 5.4 6.2 | — | 15.4 |
| | | | | found | 52.4 | 3.6 | 18.5 | 4.8 6.0 | — | 14.6 |
| | | | | $C_{22}H_{17}O_6N_2SBr$ | | | M = 517 | | | |
| 65 | Br-thienyl-CH₂ | O | 190–191 | calc. | 49.5 | 3.2 | 15.0 | 5.3 12.0 | — | 15.0 |
| | | | | found | 50.7 | 3.5 | 14.8 | 5.2 11.4 | — | 14.6 |
| | | | | $C_{22}H_{17}O_5N_2S_2Br$ | | | M = 533 | | | |
| 66 | CH₃-thienyl-CH₂ | O | 189–190 | calc. | 59.0 | 4.3 | 17.1 | 6.0 13.7 | | |
| | | | | found | 59.1 | 4.4 | 17.1 | 6.3 13.4 | | |
| | | | | $C_{23}H_{20}O_5N_2S_2$ | | | M = 468.5 | | | |
| 67 | CH₃-furyl-CH₂ | O | 167–168 | calc. | 61.4 | 4.7 | 21.1 | 6.1 7.2 | | |
| | | | | found | 61.1 | 4.4 | 21.2 | 6.2 7.1 | | |
| | | | | $C_{23}H_{20}O_6N_2S$ | | | M = 452 | | | |
| 68 | Br-thienyl-CH₂ | S | 202–203 | calc. | 48.1 | 3.1 | 11.7 | 5.1 17.5 | — | 14.5 |
| | | | | found | 48.1 | 3.2 | 11.7 | 5.1 17.1 | — | 15.0 |
| | | | | $C_{22}H_{17}O_4N_2S_3Br$ | | | | | | |
| 69 | furyl-CH₂ | O | 166–167 | calc. | 60.3 | 4.1 | 21.9 | 6.4 7.3 | | |
| | | | | found | 60.2 | 4.3 | 21.9 | 6.6 7.3 | | |
| | | | | $C_{22}H_{18}O_6N_2S$ | | | M = 438 | | | |
| 70 | Br-furyl-CH₂ | NH | 189–190 | calc. | 50.3 | 3.6 | 16.7 | 8.0 6.1 | — | 15.2 |
| | | | | found | 50.5 | 3.9 | 16.6 | 7.9 6.0 | — | 15.0 |
| | | | | $C_{22}H_{18}O_5N_3SBr \times 0.5\ H_2O$ | | | | | | |
| 71 | thienyl-CH₂ | NH | 201–202 | calc. | 58.3 | 4.2 | 14.1 | 9.3 14.1 | | |
| | | | | found | 58.4 | 4.4 | 14.3 | 9.5 14.0 | | |
| | | | | $C_{22}H_{19}O_4N_3S_2$ | | | M = 454 | | | |

EXAMPLE 72

Formula 1:

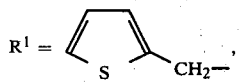

$R^1 = $ thienyl-CH₂—, $R^2$=H, $R^3$=H, X=SO, Ar=$C_6H_5$.

Starting from the compound from Example 62, the above substance was prepared by a procedure similar to general procedure D. Yield: 75%.

Melting point: 199°–201° C.

| $C_{22}H_{18}O_5N_2S_3$ | | M = 486.6 | | |
|---|---|---|---|---|
| | C | H | O | N | S |
| calculated: | 54.3 | 3.7 | 16.4 | 5.7 | 19.7 |
| found: | 54.1 | 3.8 | 16.6 | 5.7 | 19.3 |

EXAMPLE 73

3-Benzoylamino-4-phenylthio-5-pyrrol-1-yl-sulfonyl-benzoic acid methyl ester (a) 4-Chloro-5-chlorosulfonyl-3-nitro-benzoic acid methyl ester Formula 5: Y and Z=Cl, $R^3$=CH₃

50 g of 4-chloro-5-chlorosulfonyl-3-nitro-benzoic acid (J. Med. Chem. 13, 1071 (1970)) in 600 ml of half-concentrated methanolic HCl solution are stirred overnight at room temperature. After concentrating the mixture to 100 ml under reduced pressure, the product which has precipitated is filtered off and repeatedly washed with ether. 4-Chloro-5-chlorosulfonyl-3-nitrobenzoic acid methyl ester of melting point 92°–94° C. is obtained. Yield: 78%.

| $C_8H_5Cl_2NO_6S$ | | M = 314 | | | |
|---|---|---|---|---|---|
| Analysis: | C | H | Cl | N | O | S |
| calculated: | 30.6 | 1.6 | 22.5 | 4.4 | 30.6 | 10.2 |
| found: | 30.7 | 1.9 | 22.2 | 4.4 | 30.9 | 10.0 |

(b) 4-Chloro-3-nitro-5-pyrrol-1-yl-sulfonyl-benzoic acid methyl ester

Formula 7: Z=Cl, R$^3$=CH$_3$ 10 g of metallic potassium, followed by a solution of 21 ml of pyrrole in 50 ml of THF, are added to 1 liter of absolute tetrahydrofuran (THF). The mixture is refluxed until the potassium has disappeared. When the mixture has cooled to room temperature, a solution of 62 g of 4-chloro-5-chloro-sulfonyl-3-nitro-benzoic acid methyl ester in 500 ml of THF is added dropwise in the course of 30–60 minutes, and the batch is then stirred overnight at room temperature. The solvent is then substantially stripped off under reduced pressure at 30°–35° C., water is added to the residue and this mixture is extracted twice with ethyl acetate. The organic phase is dried over sodium sulfate, then boiled up with active charcoal, and filtered. The product precipitates on concentrating the filtrate under reduced pressure. After filtration, 4-chloro-3-nitro-5-pyrrol-1-yl-sulfonyl-benzoic acid methyl ester of melting point 136°–137° C. is obtained.

Yield: 70%

| C$_{12}$H$_9$ClN$_2$O$_6$S | M = 345 | | | | |
|---|---|---|---|---|---|
| Analysis: | C | H | Cl | N | O | S |
| calculated: | 41.8 | 2.6 | 10.2 | 8.1 | 27.8 | 9.3 |
| found: | 42.0 | 2.8 | 10.0 | 8.3 | 27.4 | 9.1 |

(c) 3-Nitro-4-phenylthio-5-pyrrol-1-yl-sulfonyl-benzoic acid methyl ester

Formula 8: R$^3$=CH$_3$, X=S, Ar=C$_6$H$_5$

A solution of 24.5 ml of thiophenol in 100 ml of anhydrous THF is added to a suspension of 13 g of sodium methylate in 440 ml of absolute THF whilst stirring at room temperature under nitrogen. 72 g of 4-chloro-3-nitro-5-pyrrol-1-yl-sulfonylbenzoic acid methyl ester in 220 ml of absolute THF are then added dropwise and the mixture is stirred at room temperature until the end of the reaction is reached, as ascertained by thin layer chromatography. After removing the solvent on a rotary evaporator, the residue is repeatedly extracted with hexane and then recrystallized from ethyl acetate/methanol. 3-Nitro-4-phenylthio-5-pyrrol-1-yl-sulfonyl-benzoic acid methyl ester of melting point 153°–154° C. is obtained. Yield: 45%.

| C$_{18}$H$_{14}$N$_2$O$_6$S$_2$ | M = 418 | | | | |
|---|---|---|---|---|---|
| Analysis: | C | H | N | O | S |
| calculated: | 51.6 | 3.3 | 6.6 | 22.9 | 15.3 |
| found: | 51.7 | 3.6 | 6.8 | 22.7 | 14.9 |

(d) 3-Amino-4-phenylthio-5-pyrrol-1-yl-sulfonylbenzoic acid methyl ester

Formula 9: R$^3$=CH$_3$, X=S, Ar=C$_6$H$_5$ 20 g of 3-nitro-4-phenylthio-5-pyrrol-1-yl-sulfonylbenzoic acid methyl ester in 1 liter of ethyl acetate are hydrogenated in the presence of 2 g of palladium on active charcoal, initially at room temperature and then at 40°–50° C. After filtering off the catalyst and concentrating the filtrate under reduced pressure, the residue is chromatographed over a silica gel column, using methylene chloride. The fractions containing the desired product are freed from solvent and the residue is recrystallized from methanol. 3-Amino-4-phenylthio-5-pyrrol-1-yl-sulfonylbenzoic acid methyl ester of melting point 118°–119° C. is obtained.

Yield: 80%.

| C$_{18}$H$_{16}$N$_2$O$_4$S$_2$ | M = 388.5 | | | | |
|---|---|---|---|---|---|
| Analysis: | C | H | N | O | S |
| calculated: | 55.6 | 4.1 | 7.2 | 16.5 | 16.5 |
| found: | 55.7 | 3.9 | 7.2 | 16.8 | 16.3 |

(e) 3-Benzoylamino-4-phenylthio-5-pyrrol-1-yl-sulfonyl-benzoic acid methyl ester Formula 4: R$^3$=CH$_3$, X=S, Ar=C$_6$H$_5$, R$^6$=C$_6$H$_5$ 1.4 ml of pyridine, and a solution of 7.2 g of benzoyl chloride in 30 ml of acetone, are added to 5 g of 3-amino-4-phenylthio-5-pyrrol-1-yl-sulfonylbenzoic acid methyl ester, dissolved in 25 ml of anhydrous dioxane, and the mixture is stirred at room temperature and subsequently at 40° C. The solvent is stripped off under reduced pressure, the residue is taken up in methylene chloride and the solution is washed with dilute sodium bicarbonate solution. After drying the solution over sodium sulfate, the solvent is stripped off on a rotary evaporator and the residue is recrystallized from methanol/methylene chloride. 3-Benzoylamino-4-phenylthio-5-pyrrol-1-yl-sulfonylbenzoic acid methyl ester of melting point 210°–211° C. is obtained. Yield: 59%.

| C$_{25}$H$_{20}$N$_2$O$_5$S$_2$ | M = 492.6 | | | | |
|---|---|---|---|---|---|
| Analysis: | C | H | N | O | S |
| calculated: | 61.0 | 4.1 | 5.7 | 16.2 | 13.0 |
| found: | 61.2 | 4.4 | 5.8 | 16.3 | 12.8 |

EXAMPLES 74–76

Following procedure (e) in Example 73, the compounds shown below are prepared from the compounds of the general formula 9 (R$^3$=CH$_3$, Ar=C$_6$H$_5$), yields of 55–93% being achieved.

| | | Formula 4 (R$^3$ = CH$_3$, Ar = C$_6$H$_5$) | | | | | | |
|---|---|---|---|---|---|---|---|---|
| Example No. | R$^6$ | X | Melting point, °C. | | Analysis | | | |
| | | | | | C | H | O | N | S |
| 74 | C$_6$H$_5$ | NH | 191–192 | calc. | 63.1 | 4.5 | 16.8 | 8.8 | 6.7 |
| | | | | found | 63.0 | 4.5 | 16.7 | 8.9 | 6.7 |
| | | | | C$_{25}$H$_{21}$O$_5$N$_3$S | | M = 476 | | | |

-continued

Formula 4 ($R^3 = CH_3$, Ar = $C_6H_5$)

| Example No. | $R^6$ | X | Melting point, °C. | Analysis | | | | | |
|---|---|---|---|---|---|---|---|---|---|
| | | | | | C | H | O | N | S |
| 75 |  | S | 165–167 | calc. | 57.2 | 3.7 | 19.9 | 5.8 | 13.3 |
| | | | | found | 57.5 | 3.8 | 19.6 | 5.7 | 13.1 |
| | | | | $C_{23}H_{18}O_6N_2S_2$ | | | M = 482.5 | | |
| 76 |  | NH | 182–183 | calc. | 59.3 | 4.1 | 20.6 | 9.0 | 6.9 |
| | | | | found | 59.1 | 4.2 | 20.1 | 9.2 | 6.9 |
| | | | | $C_{23}H_{19}O_6N_3S$ | | | M = 465 | | |
| 77 |  | NH | 193–194 | calc. | 57.4 | 4.0 | 16.6 | 8.7 | 13.3 |
| | | | | found | 57.0 | 4.1 | 16.8 | 8.9 | 13.1 |
| | | | | $C_{23}H_{19}O_5N_3S_2$ | | | M = 482 | | |
| 78 |  | O | 224–225 | calc. | 54.8 | 3.9 | 26.9 | 6.7 | 7.7 |
| | | | | found | 54.4 | 3.9 | 26.8 | 6.8 | 7.6 |
| | | | | $C_{19}H_{16}O_7N_2S$ | | | M = 416 | | |

EXAMPLE 79

3-(2-Furfuroylamino)-4-phenylthio-5-pyrrol-1-yl-sulfonylbenzoic acid methyl ester Formula 4: $R^3 = CH_3$, X=S, Ar=$C_6H_5$, $R^6 =$ 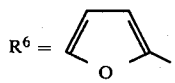

3.4 g of 2-furfuroyl chloride, dissolved in 30 ml of dioxane, are added dropwise to a solution of 5 g of 3-amino-4-phenylthio-5-pyrrol-1-yl-sulfonylbenzoic acid methyl ester and 1.4 ml of N,N-dimethylaniline in 25 ml of anhydrous dioxane. After it has been stirred for 3–8 hours at room temperature, the mixture is concentrated under reduced pressure, the residue is dissolved in methylene chloride and the organic phase is washed with water and dilute sodium bicarbonate solution, dried over sodium sulfate, and freed from the solvent on a rotary evaporator. After recrystallizing the residue from methylene chloride/methanol, 5 g of 3-(2-furfuroylamino)-4-phenylthio-5-pyrrol-1-yl-sulfonylbenzoic acid methyl ester of melting point 165°–167° C. are obtained.

Yield: 87%.

EXAMPLES 80 TO 84

The compounds shown below are obtained, in yields of 75–96%, from the compounds of the general formula 9 ($R^3=CH_3$, Ar=$C_6H_5$), by a procedure similar to that of Example 79.

| Example No. | $R^6$ | X | Melting point, °C. | Analysis | | | | | | |
|---|---|---|---|---|---|---|---|---|---|---|
| | | | | | C | H | O | N | S | Br |
| 80 |  | S | 196–197 | calc. | 55.4 | 3.6 | 16.0 | 5.6 | 19.3 | |
| | | | | found | 55.3 | 3.7 | 15.8 | 5.6 | 18.9 | |
| | | | | $C_{23}H_{18}N_2O_5S_2$ | | | | M = 499 | | |
| 81 |  | NH | 185–186 | calc. | 57.4 | 4.0 | 16.6 | 8.7 | 13.3 | |
| | | | | found | 57.3 | 3.9 | 16.6 | 9.0 | 13.2 | |
| | | | | $C_{23}H_{19}O_5N_3S_2$ | | | | M = 482 | | |
| 82 |  | NH | 160–161 | calc. | 59.3 | 4.1 | 20.6 | 9.0 | 6.9 | |
| | | | | found | 59.0 | 4.1 | 20.3 | 9.1 | 6.8 | |
| | | | | $C_{23}H_{19}N_3O_6S$ | | | | M = 465.6 | | |
| 83 | 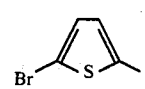 | S | 187–188 | calc. | 47.8 | 3.0 | 13.8 | 4.9 | 16.7 | |
| | | | | found | 48.1 | 3.3 | 13.8 | 4.9 | 16.4 | |
| | | | | $C_{23}H_{17}O_5N_2S_3Br$ | | | | M = 577 | | |

-continued

| Example No. | R⁶ | X | Melting point, °C. | Analysis | | | | | |
|---|---|---|---|---|---|---|---|---|---|
| | | | | | C | H | O N | S | Br |
| 84 | (Br-furyl-methyl) | NH | 177–178 | calc. | 50.7 | 3.3 | 17.6  7.7 | 5.9 | 14.7 |
| | | | | found | 50.6 | 3.5 | 17.0  7.8 | 5.8 | 15.0 |
| | | | | $C_{23}H_{18}O_6N_3SBr$ | | | $M = 544$ | | |

EXAMPLE 85

3-Benzoylamino-4-phenylthio-5-(pyrrol-1-yl-sulfonyl)-benzoic acid methyl ester (a) 3-Amino-4-chloro-5-(pyrrol-1-yl-sulfonyl)-benzoic acid methyl ester Formula 13: $R^3=CH_3$, $Z=Cl$ A solution of 55 g of 4-chloro-3-nitro-5-(pyrrol-1-yl-sulfonyl)-benzoic acid methyl ester (see Example 73 b) in 800 ml of ethyl acetate is hydrogenated in the presence of 5.0 g of 10% strength palladium on active charcoal, at 20°–40° C., until the absorption of hydrogen has ceased (which requires about 7 hours). After separating off the catalyst, the filtrate is freed from the solvent and the residue is recrystallized from a 9:1 ethyl acetate/methanol mixture. 3-Amino-4-chloro-5-(pyrrol-1-yl-sulfonyl)-benzoic acid methyl ester of melting point 178°–181° C. is obtained.

Yield: 70%.

| $C_{12}H_{11}N_2O_4SCl$ | | $M = 314.75$ | | | | |
|---|---|---|---|---|---|---|
| Analysis: | C | H | N | O | S | Cl |
| calculated: | 45.8 | 3.5 | 8.9 | 20.3 | 10.2 | 11.3 |
| found: | 45.3 | 3.4 | 8.9 | 20.8 | 9.9 | 11.2 |

(b) Benzoylamino-4-chloro-5-(pyrrol-1-yl-sulfonyl)-benzoic acid methyl ester

Formula 14: $R^3=CH_3$, $Z=Cl$, $R^6=C_6H_5$.

3.2 ml of pyridine are added to a solution of 10.0 g of 3-amino-4-chloro-5-(pyrrol-1-sulfonyl)-benzoic acid methyl ester in 64 ml of anhydrous dioxane, and a solution of 8.9 g of benzoyl chloride in 64 ml of acetone is then added dropwise at room temperature. The mixture is stirred at room temperature overnight and is then concentrated under reduced pressure, and the residue is taken up in ethyl acetate. After washing the solution twice with water, the organic phase is dried over sodium sulfate and freed from the solvent on a rotary evaporator. After recrystallization from methanol, 6.4 g of 3-benzoyl-amino-4-chloro-5-(pyrrol-1-yl-sulfonyl)-benzoic acid methyl ester of melting point 181°–182° C. are obtained.

Yield: 61%.

| $C_{19}H_{15}ClN_2O_5S$ | | $M = 418.9$ | | | |
|---|---|---|---|---|---|
| Analysis: | C | H | Cl | N | S |
| calculated: | 54.4 | 3.6 | 8.5 | 6.7 | 7.7 |
| found: | 54.3 | 3.4 | 8.5 | 7.0 | 7.7 |

(c) 3-Benzoylamino-4-phenylthio-5-(pyrrol-1-yl-sulfonyl)-benzoic acid methyl ester Formula 4: $R^3=CH_3$, $X=S$, $R^6$ and $Ar=C_6H_5$ This compound is prepared in accordance with procedure (c) of Example 73, from 87.4 g of the compound obtained above (Example 85 b). The product is recrystallized from methanol/methylene chloride. Melting point: 210°–211° C.

Yield: 93%.

The compounds of Examples 86 and 87 are obtained from compounds of the formula 17 ($R^3=H$, $E=NO_2$) by catalytic hydrogenation, using a procedure similar to that described for Example 85 (a).

Formula 17: $R^3=H$, $E=NH_2$.

| Example No. | D | Melting point °C. |
|---|---|---|
| 86 | $SC_6H_5$ | 212–216 |
| 87 | $NHC_6H_5$ | 282–284 |

EXAMPLE 88

3-Benzoylamino-4-chloro-5-(pyrrol-1-yl-sulfonyl)-benzoic acid methyl ester

Formula 16: $R^3=CH_3$, $Z=Cl$, $R^2=H$, $R^1=C_6H_5-CH_2-$.

A solution of 0.14 g of $NaBH_4$ in 5 ml of dry diglyme is added dropwise at room temperature to a solution of 1.0 g of 3-benzoylamino-4-chloro-5-(pyrrol-1-yl-sulfonyl)-benzoic acid methyl ester in 10 ml of dry diglyme and 0.6 ml of $BF_3$-etherate. After 1 hour, the excess $NaBH_4$ is destroyed with a small amount of $H_2O$, the precipitate is filtered off and about 20 ml of water are added to the filtrate, whilst cooling. The product which has precipitated is filtered off and washed once with water and then with n-hexane. After recrystallization from methanol, the pure product of melting point 143°–145° C. is obtained.

Yield: 90%.

| $C_{19}H_{17}N_2O_4SCl$ | | $M = 404.87$ | | | |
|---|---|---|---|---|---|
| Analysis: | C | H | N | O | S | Cl |
| calculated: | 56.4 | 4.2 | 6.9 | 15.8 | 7.9 | 8.7 |
| found: | 56.4 | 4.4 | 7.0 | 16.2 | 7.9 | 8.7 |

The compounds of Examples 89 to 100, shown below, are obtained in yields of 50–90% by reacting a compound of the formula 18 in accordance with the general procedure A or B specified earlier.

Formula 17

| Example No. | R³ | D | E | General procedure | Melting point, °C. |
|---|---|---|---|---|---|
| 89 | H | Cl | NO₂ | A | 223–225 |
| 90 | H | Cl | NO₂ | B | " |
| 91 | CH₃ | Cl | NO₂ | A | 138–140 |
| 92 | H | SC₆H₅ | NO₂ | B | 241–243 |
| 93 | H | NHC₆H₅ | NO₂ | B | 264–267 |
| 94 | CH₃ | Cl | C₆H₅CONH | A | 182–183 |
| 95 | H | OC₆H₅ | NO₂ | A | 180–182 |
| 96 | CH₃ | OC₆H₅ | (5-bromo-furan-2-CONH) | A | 201–202 |
| 97 | CH₃ | OC₆H₅ | (5-bromo-furan-2-CONH) | A | 206–208 |
| 98 | CH₃ | OC₆H₅ | (5-bromo-3-methyl-thiophene-2-CONH) | A | 206–208 |
| 99 | CH₃ | OC₆H₅ | (5-methyl-furan-2-CONH) | A | 199–201 |
| 100 | CH₃ | OC₆H₅ | (furan-2-CONH) | A | 189–190 |

EXAMPLES 101 TO 104

The starting compounds of Examples 96–98 are prepared from 3-amino-4-phenoxy-5-sulfamyl-benzoic acid methyl ester by acylation, following a procedure similar to Example 79, yields of 70–93% being obtained.

Formula 18 (R³ = CH₃, D = OC₆H₅)

| Example No. | E | Melting point, °C. | Analysis | C | H | O | N | S | Br |
|---|---|---|---|---|---|---|---|---|---|
| 101 | 5-bromo-furan-2-CONH | 241–243 | calc. | 46.1 | 3.0 | 22.6 | 5.7 | 6.5 | 16.1 |
|  |  |  | found | 46.7 | 3.5 | 23.3 | 5.5 | 5.9 | 15.0 |
|  |  |  | C₁₉H₁₅O₇N₂SBr | M = 495 | | | | | |
| 102 | 5-bromo-thiophene-2-CONH | 236–237 | calc. | 44.6 | 3.0 | 18.8 | 5.5 | 12.5 | 15.6 |
|  |  |  | found | 45.7 | 3.6 | 20.0 | 5.2 | 11.4 | 14.6 |
|  |  |  | C₁₉H₁₅O₆N₂S₂Br | M = 511 | | | | | |
| 103 | 3-methyl-thiophene-2-CONH | 221–222 | calc. | 53.8 | 4.0 | 21.5 | 6.3 | 14.3 | — |
|  |  |  | found | 53.6 | 4.0 | 22.1 | 6.4 | 14.0 | — |
|  |  |  | C₂₀H₁₈O₆N₂S₂ | M = 446 | | | | | |
| 104 | 5-methyl-furan-2-CONH | 208–209 | calc. | 55.8 | 4.2 | 26.0 | 6.5 | 7.5 | — |
|  |  |  | found | 55.9 | 4.9 | 26.8 | 6.2 | 6.9 | — |
|  |  |  | C₂₀H₁₈O₇N₂S | M = 430 | | | | | |

The compounds of Examples 105 to 109 are obtained in accordance with general procedure C, the starting material in Examples 105 to 107 being a compound of the general formula 17 (R³=H) and in Examples 108 and 109 a compound of the general formula 9 (R³=H). Yields: 80–95%.

Formula 17: R³ = CH₃

| Example No. | E | D | Melting point °C. |
|---|---|---|---|
| 105 | NO₂ | Cl | 138–140 |
| 106 | NO₂ | SC₆H₅ | 154–157 |
| 107 | NO₂ | NHC₆H₅ | 135–136 |

Formula 9: R³ = CH₃

| Example No. | E | D | Melting point °C. |
|---|---|---|---|
| 108 | NH₂ | SC₆H₅ | 118–119 |
| 109 | NH₂ | NHC₆H₅ | 144–146 |

Formula 2 (R², R³ = H)

| Example No. | R¹ | X | Ar | Melting point °C. | Analysis | C | H | O | S | N | Br |
|---|---|---|---|---|---|---|---|---|---|---|---|
| 110 | o-Br—C₆H₄CH₂— | S | C₆H₅ | 223–225 | calc. | 48.7 | 3.5 | 13.0 | 13.0 | 5.7 | 16.2 |
|  |  |  |  |  | found | 48.5 | 3.7 | 13.2 | 12.8 | 5.8 | 16.3 |
|  |  |  |  |  | C₂₀H₁₇O₄N₂S₂Br | M = 493 | | | | | |
| 111 | p-CN—C₆H₄—CH₂— | S | C₆H₅ | 270–272 | calc. | 57.4 | 3.9 | 14.6 | 14.5 | 9.6 | — |
|  |  |  |  |  | found | 57.3 | 4.0 | 15.0 | 14.4 | 10.0 | — |

-continued

| | | | | | | | | | | | |
|---|---|---|---|---|---|---|---|---|---|---|---|
| | | | | | | $C_{21}H_{17}O_4N_3S_2$ | | M = 440 | | | |
| 112 | p-CO$_2$H—C$_6$H$_4$—CH$_2$— | S | C$_6$H$_5$ | 303–304 | calc. | 55.0 | 3.9 | 20.9 | 13.9 | 6.1 | — |
| | | | | | found | 54.8 | 4.2 | 21.1 | 13.7 | 6.2 | — |
| | | | | | | $C_{21}H_{18}O_6N_2S_2$ | | M = 459 | | | |
| 113 | m-CH$_3$—C$_6$H$_4$—CH$_2$ | S | C$_6$H$_5$ | 211–212 | calc. | 58.8 | 4.7 | 14.9 | 14.9 | 6.5 | — |
| | | | | | found | 58.8 | 4.7 | 15.0 | 14.7 | 6.8 | — |
| | | | | | | $C_{21}H_{20}O_4N_2S_2$ | | | | | |

II. The halothiophene compounds used in Examples 33, 36 and 37 can be obtained as follows.

EXAMPLE 1

300 ml of isopropanol, 300 ml of H$_2$O and 200 g of 2,3-dichloro-thiophene-4-aldehyde are introduced into a 2 liter flask and 16 g of NaBH$_4$ are added in portions over 45 minutes. The reaction is exothermic, and is carried out with cooling at 35°–40° C. Thereafter, the two-phase mixture is stirred for 30 minutes at the same temperature, and 300 ml of H$_2$O and 500 ml of CH$_2$Cl$_2$ are then added. After phase separation, the aqueous phase is re-extracted twice with 250 ml of CH$_2$Cl$_2$. The organic phases are washed with 250 ml of H$_2$O and concentrated. The oily residue is taken up in cyclohexane, whereupon 182 g of 2,3-dichloro-4-hydroxymethyl-thiophene are obtained in a crystalline form (87.3% of theory). Melting point 63°–65° C.

EXAMPLE 2

124 g of 2-chloro-thiophene-4-aldehyde in 200 ml of isopropanol and 200 ml of H$_2$O are reduced with 12 g of NaBH$_4$, and worked up, using the method described in Example II, 1. The reaction product is purified by distillation and gives, in addition to 20 g of first runnings and tailings, 83 g of 2-chloro-4-hydroxymethyl-thiophene, i.e. 77% of theory; melting point 67°–69° C./0.3 mm Hg.

EXAMPLE 3

The following are prepared by a method similar to that of Example II, 1:

| | Boiling point/ melting point | Yield |
|---|---|---|
| 2-Bromo-4-hydroxymethyl-thiophene | 86–88° C./0.4 mm Hg | 91% |
| 2,3-Dibromo-4-hydroxymethyl-thiophene | 79–82° C. | 83% |

EXAMPLE 4

A mixture of 549 g of 2,3-dichloro-4-hydroxymethyl-thiophene and 450 ml of CHCl$_3$ is introduced into a 1 liter flask and cooled to 0° C., and a mixture of 271 g of PBr$_3$ and 50 ml of CHCl$_3$ is added in the course of 1 hour, at 0°–5° C. The solution is stirred for a further hour and is then poured onto ice. After separating off the organic phase, the aqueous phase is re-extracted twice with a small amount of ether. The organic phases are concentrated under reduced pressure and the residue is distilled in the presence of a small amount of triethylamine at 58°–60° C./0.1 mm Hg.

The following bromomethylthiophenes are prepared analogously:

| | Boiling point | Yield |
|---|---|---|
| 2-Bromo-4-bromomethyl-thiophene | 88–90° C./0.7 mm Hg | 55% |
| 2-Chloro-4-bromomethyl-thiophene | 61–62° C./0.4 mm Hg | 75% |
| 2,3-Dibromo-4-bromomethyl-thiophene | crude product | 96% |

III. Examples 114 to 131, which follow, relate to compounds where $R^4$ and $R^5$ are lower alkyl.

General Procedure

A'. Formula 1 ($R^2$=H, $R^3$=alkyl).

A mixture of 0.02 mole of a compound of the formula 2 ($R^2$=H, $R^3$=alkyl), 0.15 g of p-toluenesulfonic acid and 0.06 mole of a compound of the formula 3a in 200 ml of dry toluene is refluxed, under a water separator. Samples are taken and subjected to thin layer chromatography to ascertain the end of the reaction. A further 0.03 mole of the compound of the formula 3a is added after from 10 to 20 hours, depending on the progress of the reaction. The total reaction time is from 0.4 to 1.5 days. When the starting compound of the formula 2 ($R^2$=H, $R^3$=alkyl) is no longer detectable by thin layer chromatography, the reaction mixture is concentrated to dryness under reduced pressure. Depending on the purity of the crude product, the compound obtained, of the formula 1 ($R^2$=H, $R^3$=alkyl) is isolated by recrystallization from methanol/methylene chloride or acetone or by column chromatography over silica gel, using methylene chloride as the mobile phase. The yields are from 50 to 95%.

B'. Formula 1 ($R^2$=H, $R^3$=H).

A solution of 11 millimoles of sodium hydroxide in 140 ml of water is added to a solution of 10 millimoles of a compound of the formula 1 ($R^2$=H, $R^3$=alkyl) in 250 ml of ethanol. The reaction mixture is refluxed for 3 hours. The alcohol is then distilled off and the aqueous residue is acidified to pH 1 with 2 N hydrochloric acid.

The product of the formula 1 ($R^3$=H), which has precipitated, is filtered off and dried. Yield: 95–99%.

The compounds referred to in Examples 114 to 131 below were prepared in accordance with these procedures III. A' and III. B'.

| | | Formula 1 ($R^2$ and $R^3$ = H, Ar = $C_6H_5$) | | | | | | | | |
|---|---|---|---|---|---|---|---|---|---|---|
| Example No. | $R^1$ | α-$R^4$ | α'-$R^5$ | X | Melting point [°C.] | Analysis | C | H | O | N | S |
| 114 | ⟨S⟩–$CH_2$– | $C_2H_5$ | $C_2H_5$ | O | 189–190 | calc. | 61.2 | 5.1 | 15.7 | 5.5 | 12.6 |
| | | | | | | found | 61.5 | 5.3 | 15.6 | 5.5 | 12.1 |
| | | | | | $C_{26}H_{26}O_5N_2S_2$ | M = 511 | | | | | |
| 115 | " | $CH_3$ | $CH_2CH_2CH_3$ | O | 170–173 | calc. | 61.2 | 5.1 | 15.7 | 5.5 | 12.6 |
| | | | | | | found | 60.9 | 5.0 | 15.7 | 5.4 | 12.2 |
| | | | | | $C_{26}H_{26}O_5N_2S_2$ | M = 511 | | | | | |
| 116 | " | $CH_3$ | $C_2H_5$ | O | 200–201 | calc. | 60.5 | 4.9 | 16.1 | 5.6 | 12.5 |
| | | | | | | found | 60.5 | 5.0 | 16.1 | 5.9 | 12.7 |
| | | | | | $C_{25}H_{24}O_5N_2S_2$ | M = 497 | | | | | |
| 117 | " | $CH_3$ | $CH_3$ | S | 187–189 | calc. | 57.8 | 4.5 | 12.8 | 5.6 | 19.3 |
| | | | | | | found | 57.6 | 4.5 | 13.1 | 5.7 | 18.6 |
| | | | | | $C_{24}H_{22}O_4N_2S_3$ | M = 498.6 | | | | | |
| 118 | " | $CH_3$ | $CH_3$ | O | 200–201 | calc. | 59.7 | 4.6 | 16.6 | 5.8 | 13.3 |
| | | | | | | found | 59.7 | 4.6 | 16.5 | 6.0 | 13.2 |
| | | | | | $C_{24}H_{22}O_5N_2S_2$ | M = 483 | | | | | |
| 119 | " | $CH_3$ | $C_2H_5$ | S | 200–202 | calc. | 58.6 | 4.7 | 12.5 | 5.5 | 18.6 |
| | | | | | | found | 59.0 | 4.9 | 12.5 | 5.4 | 18.2 |
| | | | | | $C_{25}H_{24}O_4N_2S_3$ | M = 513 | | | | | |
| 120 | " | $CH_3$ | $CH_3$ | NH | 225–226 | calc. | 59.9 | 4.8 | 13.3 | 8.7 | 13.3 |
| | | | | | | found | 59.7 | 5.0 | 13.1 | 8.9 | 13.5 |
| | | | | | $C_{24}H_{23}O_4N_3S_2$ | M = 482 | | | | | |
| 121 | $C_6H_5$—$CH_2$ | $CH_3$ | $CH_3$ | S | 221–223 | calc. | 63.4 | 4.9 | 13.0 | 5.7 | 13.0 |
| | | | | | | found | 63.5 | 5.0 | 13.0 | 5.7 | 12.0 |
| | | | | | $C_{26}H_{24}O_4N_2S_2$ | M = 492.6 | | | | | |
| 122 | " | $CH_3$ | $CH_3$ | O | 159–160 | calc. | 65.5 | 5.1 | 16.8 | 5.9 | 6.7 |
| | | | | | | found | 65.6 | 5.1 | 16.7 | 6.0 | 6.7 |
| | | | | | $C_{26}H_{24}O_5N_2S$ | M = 477 | | | | | |
| 123 | " | $CH_3$ | $CH_3$ | NH | 220–222 | calc. | 65.7 | 5.3 | 13.5 | 8.8 | 6.7 |
| | | | | | | found | 65.7 | 5.2 | 13.4 | 9.0 | 6.6 |
| | | | | | $C_{26}H_{25}N_3O_4S$ | M = 476 | | | | | |
| 124 | " | $CH_3$ | $C_2H_5$ | NH | 178–180 | calc. | 66.4 | 5.4 | 13.1 | 8.6 | 6.6 |
| | | | | | | found | 65.7 | 5.7 | 13.3 | 8.6 | 6.2 |
| | | | | | $C_{27}H_{26}O_4N_3S$ | M = 489 | | | | | |
| 125 | $C_6H_5$—$CH_2$ | $CH_3$ | $C_2H_5$ | S | 194–196 | calc. | 64.0 | 5.2 | 12.6 | 5.5 | 12.7 |
| | | | | | | found | 64.1 | 5.5 | 12.7 | 5.6 | 12.3 |
| | | | | | $C_{27}H_{26}O_4N_2S_2$ | M = 507 | | | | | |
| 126 | $CH_2CH_2CH_2CH_3$ | $CH_3$ | $CH_3$ | O | 160–162 | calc. | 62.4 | 5.9 | 18.1 | 6.3 | 7.2 |
| | | | | | | found | 62.4 | 5.8 | 18.2 | 6.3 | 7.2 |
| | | | | | $C_{23}H_{26}O_5N_2S$ | M = 443 | | | | | |
| 127 | " | $CH_3$ | $CH_3$ | S | 146 | calc. | 60.2 | 5.7 | 14.0 | 6.1 | 14.0 |
| | | | | | | found | 59.4 | 5.8 | 15.0 | 6.1 | 13.5 |
| | | | | | $C_{23}H_{26}O_4N_2S_2$ | M = 459 | | | | | |
| 128 | ⟨S⟩–$CH_2$– | $CH_3$ | $CH_3$ | S | 201 | calc. | 57.8 | 4.5 | 12.8 | 5.6 | 19.3 |
| | | | | | | found | 57.6 | 4.6 | 13.1 | 5.7 | 18.6 |
| | | | | | $C_{24}H_{22}O_4N_2S_3$ | M = 499 | | | | | |
| 129 | " | $CH_3$ | $CH_3$ | O | 184–186 | calc. | 59.7 | 4.6 | 16.6 | 5.8 | 13.3 |
| | | | | | | found | 59.5 | 4.5 | 16.4 | 5.6 | 13.6 |
| | | | | | $C_{24}H_{22}O_5N_2S_2$ | M = 483 | | | | | |
| 130 | " | $CH_3$ | $CH_3$ | NH | 214–216 | calc. | 59.8 | 4.8 | 13.8 | 8.7 | 13.3 |
| | | | | | | found | 59.7 | 4.8 | 13.2 | 8.8 | 13.4 |
| | | | | | $C_{24}H_{23}O_4N_3S_2$ | M = 482 | | | | | |
| 131 | ⟨O⟩–$CH_2$– | $CH_3$ | $CH_3$ | NH | 211–213 | calc. | 61.9 | 5.0 | 17.2 | 9.0 | 6.9 |
| | | | | | | found | 61.7 | 5.1 | 17.3 | 9.2 | 6.7 |
| | | | | | $C_{24}H_{23}O_5N_3S$ | M = 465.5 | | | | | |

IV. Examples of formulations.

1. Tablets of the following composition are pressed in the conventional manner on a tableting press:

30 mg of 3-N-phenylamino-4-phenoxy-5-(2,5-dimethyl-pyrrol-1-yl-sulfonyl)-benzoic acid
150 mg of corn starch
13.50 mg of gelatin
45 mg of lactose
22.5 mg of talc
2.25 mg of Aerosil$^R$ (chemically pure silica in a submicroscopic state of division)
6.75 mg of potato starch (as a 6% paste)

EXAMPLE 2

Dragees of the following composition are prepared in the conventional manner:

20 mg of 3-N-benzylamino-4-phenoxy-5-(2,5-dimethyl-pyrrol-1-yl-sulfonyl)-benzoic acid
170 mg of core composition
160 mg of sugar-coating composition The core composition consists of 9 parts of corn starch, 3 parts of lactose and 1 part of Luviskol$^R$ VA 64 (a 60:40 vinylpyrrolidone/vinyl acetate copolymer, cf. Pharm. Ind. 1962, 586). The sugar-coating composition consists of 5 parts of sucrose, 2 parts of corn starch, 2 parts of calcium carbonate and 1 part of talc. The dragees thus produced are subsequently provided with a coating resistant to gastric juices.

EXAMPLE 3

100 g of the Na salt of 3-N-benzylamino-4-phenoxy-5(2,5-dimethylpyrrol-1-yl-sulfonyl)-benzoic acid are dissolved in 5 liters of water. The solution is brought to pH 3.5 with 0.1 N sodium acetate and is rendered isotonic by adding sodium chloride. It is then packed under sterile conditions in ampoules of 2 ml capacity.

EXAMPLE 4

100 g of the Na salt of 3-N-benzylamino-4-phenoxy5-(2,5-dimethylpyrrol-1-yl-sulfonyl)-benzoic acid are dissolved in 50 liters of water, and the solution is rendered isotonic by adding glucose and is neutralized to pH 7.0. It is then packed under sterile conditions in 200 ml infusion pouches.

We claim:

1. A compound of the formula

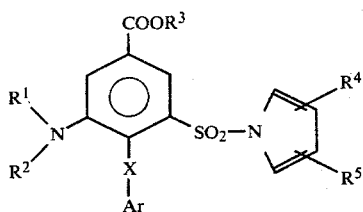

in which $R^1$ is alkyl of 2 to 5 carbon atoms, allyl, benzyl, furylmethyl, wherein the furan ring is unsubstituted or substituted by bromine, or thienylmethyl, wherein the thiophene ring is unsubstituted or monosubstituted by methyl, and $R^2$ is hydrogen, or $R^1$ and $R^2$ together with the nitrogen are a pyrrolidine ring, $R^3$ is hydrogen, methyl or ethyl, $R^4$ and $R^5$ are hydrogen or $R^4$ is methyl or ethyl in the $\alpha$-position of the pyrrole ring and $R^5$ is methyl, ethyl or n-propyl in the $\alpha'$-position of the pyrrole ring, X is sulfur or oxygen, or N–H and Ar is phenyl, which is unsubstituted or substituted by chlorine and its therapeutically useful ammonium salts, alkali metal salts or acid addition salts.

2. A compound of the formula 1 as claimed in claim 1, in which $R^1$ is n-butyl, benzyl, 3-thienylmethyl, 2-thienylmethyl, 3-furylmethyl or 2-furylmethyl, $R^2$ is hydrogen, $R^3$ is hydrogen, $R^4$ is methyl or ethyl in the $\alpha$-position to the nitrogen atom of the pyrrole ring, $R^5$ is methyl, ethyl or n-propyl in the $\alpha'$-position to the nitrogen atom in the pyrrole ring, X is sulfur, oxygen or N–H and Ar is phenyl, and its therapeutically useful ammonium salts and alkali metal salts.

3. A compound of the formula

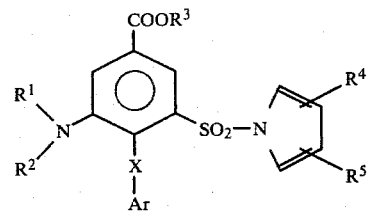

in which $R^1$ is thienylmethyl, wherein the thiophene ring is unsubstituted or monosubstituted or disubstituted by chlorine, $R^2$ is hydrogen, $R^3$ is hydrogen, methyl or ethyl, $R^4$ and $R^5$ are hydrogen or $R^4$ is methyl or ethyl in the $\alpha$-position of the pyrrole ring and $R^5$ is methyl, ethyl or n-propyl in the $\alpha'$-position of the pyrrole ring, X is sulfur or oxygen, or N–H and Ar is phenyl, which is unsubstituted or substituted by chlorine and its therapeutically useful ammonium salts, alkali metal salts or acid addition salts.

4. A compound of the formula 3 as claimed in claim 1, in which $R^1$ is 3-thienylmethyl, $R^2$ to $R^5$ are hydrogen, X is oxygen and Ar is phenyl.

5. A compound of the formula 3 as claimed in claim 1, in which $R^1$ is 3-thienylmethyl, $R^2$ and $R^3$ are hydrogen, $R^4$ and $R^5$ are $\alpha$-ethyl, X is oxygen and Ar is phenyl.

6. A compound of the formula 3 as claimed in claim 1, in which $R^1$ is 3-thienylmethyl, $R^2$ and $R^3$ are hydrogen, $R^4$ and $R^5$ are $\alpha$-methyl, X is NH and Ar is phenyl.

7. A compound of the formula 3 as claimed in claim 1, in which $R^1$ is 2-thienylmethyl, $R^2$ and $R^3$ are hydrogen, $R^4$ and $R^5$ are $\alpha$-methyl, X is oxygen and Ar is phenyl.

8. A compound of the formula 1 in claim 3 where $R^1$ is 3-thienylmethyl, $R^2$ and $R^3$ are hydrogen, $R^4$ is $\alpha$-methyl, $R^5$ is $\alpha'$-ethyl, X is oxygen and Ar is phenyl.

9. A pharmaceutical diuretic composition comprising an effective amount of a compound of the formula I of claim 1 and a pharmaceutically acceptable carrier.

* * * * *